United States Patent
Podoleanu et al.

(10) Patent No.: US 8,678,594 B2
(45) Date of Patent: Mar. 25, 2014

(54) APPARATUS AND METHOD OF MONITORING AND MEASUREMENT USING SPECTRAL LOW COHERENCE INTERFEROMETRY

(75) Inventors: Adrian Podoleanu, Kent (GB); Michael Leitner, Linz (AT)

(73) Assignee: University of Kent at Canterbury (GB)

( * ) Notice: Subject to any disclaimer, the term of this patent is extended or adjusted under 35 U.S.C. 154(b) by 437 days.

(21) Appl. No.: 12/958,791

(22) Filed: Dec. 2, 2010

(65) Prior Publication Data

US 2012/0013909 A1   Jan. 19, 2012

Related U.S. Application Data

(63) Continuation-in-part of application No. 12/835,221, filed on Jul. 13, 2010, now abandoned.

(51) Int. Cl.
| | |
|---|---|
| *A61B 3/10* | (2006.01) |
| *A61B 3/14* | (2006.01) |
| *A61B 3/12* | (2006.01) |
| *A61B 3/103* | (2006.01) |

(52) U.S. Cl.
CPC ............. *A61B 3/1225* (2013.01); *A61B 3/103* (2013.01)
USPC ........................ 351/221; 351/205; 351/206

(58) Field of Classification Search
USPC .......... 351/205, 206, 210, 221, 246; 356/450, 356/451, 456, 477–482; 382/131; 600/407, 600/425
See application file for complete search history.

(56) References Cited

U.S. PATENT DOCUMENTS

| | | | | |
|---|---|---|---|---|
| 3,599,627 | A * | 8/1971 | Millen | 600/407 |
| 4,795,253 | A * | 1/1989 | Sandridge et al. | 356/51 |
| 5,400,092 | A * | 3/1995 | Schepens et al. | 351/214 |
| 2004/0036838 | A1* | 2/2004 | Podoleanu et al. | 351/206 |
| 2005/0231727 | A1 | 10/2005 | Podoleanu | |
| 2006/0058615 | A1* | 3/2006 | Mahajan et al. | 600/407 |
| 2008/0218588 | A1 | 9/2008 | Stetten | |
| 2011/0299034 | A1* | 12/2011 | Walsh et al. | 351/206 |

OTHER PUBLICATIONS

"Channeled Spectrum Display using a CCD Array for Student Laboratory Demonstrations", published by A. Gh. Podoleanu, S. Taplin, D. J. Webb and D. A. Jackson in the European J.
A. Choma, K. Hsu J. A. Izatt, "Swept source optical coherence tomography using an all-fiber 1300-nm ring laser source," J Biomedical Optics 10_4, 044009 _ pp. 044009-1 to 0440.

(Continued)

*Primary Examiner* — Mahidere Sahle
(74) *Attorney, Agent, or Firm* — Barnes & Thornburg LLP

(57) ABSTRACT

A spectral interferometry apparatus and method are disclosed, that can be used to monitor or measure an unknown length by following a characteristic of an indicating signal. The measurement is performed by adjusting an optical path difference (OPD) in an interferometer part of an interferometer configuration until sound or light or both are obtained with the desired strength and pitch. Embodiments are presented where the unknown length is the eye length. Spectral interrogation of the interferometer optical output is achieved by reading the signal of an analogue photodetector array in a spectrometer or by tuning a swept source and processing the signal of a photodetector. Sound of different pitches are produced either directly in this process, or by using a nonlinear amplifier, or a mixer. For enhanced signal, the array may be driven by a nonlinear clock or the swept source may be driven by a distorted driving signal.

21 Claims, 16 Drawing Sheets

(56) References Cited

OTHER PUBLICATIONS

R. Huber, M. Wojtkowski, and J. G. Fujimoto, "Fourier Domain Mode Locking (FDML): A new laser operating regime and applications for optical coherence tomography," Opt. Express.

"Reflectometric fiber optic frequency-modulated continuous-wave interferometric displacement sensor" Zheng, J in Optical Engineering, vol. 44, Issue 12, Article No. 124.

* cited by examiner (a)

(b)

APPARATUS AND METHOD OF MONITORING AND MEASUREMENT USING SPECTRAL LOW COHERENCE INTERFEROMETRY

RELATED APPLICATION

This application is a continuation-in-part of co-pending U.S. patent application Ser. No. 12/835,221, filed Jul. 13, 2010.

TECHNICAL FIELD OF THE INVENTION

The present invention relates to a spectral interferometry apparatus and method, which can be used to monitor or measure an optical path difference by following a characteristic of an indicating signal.

BACKGROUND OF THE INVENTION

There is a growing interest in the application of low coherence interferometry in the general field of sensing. Low coherence interferometry methods provide absolute distance measurements and are well suited for measuring absolute or relative distances based on signal returned by rough reflecting surfaces. Spectral low coherence interferometry (LCI) methods are based on the measurement of periodicity of the channelled spectrum of the optical signal coming from a two beam interferometer. The larger the optical path difference (OPD) in the interferometer, the denser the spectral modulation of the channelled spectrum. This can be read using a spectrometer, employing a dispersing element, such as a prism or a diffraction grating, to disperse respectively diffract light on a linear photodetecting camera to transduce the channelled spectrum of the interferometer output into a temporal signal, when the interferometer is excited by a large bandwidth optical source. Alternatively, a narrow band tuneable optical source, a swept source (SS), can be employed. By tuning the optical frequency of the optical source, the channelled spectrum is scanned point by point and a temporal signal is obtained again.

Channelled spectrum methods have been used in the sensing and fibre optic sensing field. Several implementations are known, using photodetector linear arrays, such as CCD and CMOS, to interrogate the optical signal output of the sensing interferometer, which allows to scan the channelled spectrum and produce a measuring signal. Such a method and device are disclosed in "Channeled Spectrum Display using a CCD Array for Student Laboratory Demonstrations", published by A. Gh. Podoleanu, S. Taplin, D. J. Webb and D. A. Jackson in the European J. Phys., 15, (1994), p. 266-271.

The advantage of spectral methods is that the OPD information is translated into the periodicity of peaks and troughs in the channelled spectrum and no mechanical means are needed to scan the object in depth, when performing optical coherence tomography (OCT) of tissue.

If multi-layered objects are imaged, such as tissue, each layer will imprint its own channelled spectrum periodicity, depending on its depth, with the amplitude of the spectrum modulation proportional to the square root of the reflectivity of that layer. A fast Fourier transform (FFT) of the signal delivered by a linear photodetector array, a CMOS or CCD linear camera signal, translates the periodicity of the channelled spectrum into peaks of different frequencies, with the frequency directly related to the OPD value. This measurement method is called frequency domain LCI (FD-LCI). The reflectivity profile with depth obtained by FFT is termed as an A-scan. Grouping together several A-scans, a B-scan or a cross section OCT image is obtained.

If a SS is used to scan the channelled spectrum of the interferometer, then the channelled spectrum profile is obtained directly in time, as a signal delivered by a photodetector device, method called SS-LCI. The FFT of such a signal leads to an A-scan again.

The methods above present the disadvantage that information is obtained by performing FFT. This requires a processor or a PC. Also, the standard method requires a display device, usually a monitor of a PC or a Laptop. Despite the continuous progress in computing and digital signal processing, these systems and devices raise the size and cost of FD-LCI and SS-LCI systems and of their OCT counterparts, FD-OCT and SS-OCT systems.

In measurements of distances in the field, in constructions, industry, portable systems are required. To extend spectral domain—LCI measurements to such sensing and industrial applications, low cost, small size and reduced weight systems are necessary.

In ophthalmology, measurement of eye length is performed before any cataract operation. Such measurements are performed using high cost instruments. Such instruments have a large size and are expensive. There is a need for such measurements to be more accessible to small ophthalmology practices. There is also a proven need to liaise the audio signal to the value of a quantity to be measured in complex environments where the sight is concentrated on the most complex tasks, such as surgery.

The patent application US2005/023727 A1, by Podoleanu and Rogers, used a loudspeaker to indicate the strength of the interference signal in a time domain optical coherence tomography system. The audible signal strength was an indication of signal detected and was not used in any measurement of any quantity.

Patent application US2008/0218588 A1, proposes an audio signal to transmit information about a captured image. However, this audio signal is used for transmission means only and does not allow for the direct monitoring or measurement of a system parameter.

The present invention provides methods and apparatuses which can advantageously perform measurements of lengths and optical path difference using a minimum of devices which can be conveniently assembled in a small size, low weight and low cost instrument that can be operated independent of computational power, simply by following a meter indication, a needle, a digital indication, a source of light or a source of sound.

SUMMARY OF THE INVENTION

According to a first aspect of the invention there is provided a spectral interferometry method to measure an unknown length, based on an interferometer where an adjustment of an adjusting length device is performed until sound of a certain frequency is obtained. When the sound reaches maximum intensity, the value of the adjusting length provides a measure of the unknown length.

The unknown length could be that between an object and the instrument, could be that between two reflectors in a sensor, between two walls in constructions, between two parts in robotics, or the distance between the cornea and retina in an eye.

The present invention relates to a spectral interferometry apparatus and method, which can be used to monitor or measure an optical path difference by following a characteristic of an indicating signal.

In particular, the method may be Fourier domain optical low coherence interferometry (FD-LCI) or swept source optical low coherence interferometry (SS-LCI). As a further particularity, the characteristic of the indicating signal is the strength of sound and/or its pitch, or the strength of signal of a certain frequency passing through a pass band filter and determining an indication in the form of a voltage, light or sound. According to the invention, the measurement and monitoring may be performed without resorting to digital display or computational power, i.e. no PC is necessary. The method and apparatus presented may require a single adjustment until maximum is achieved for a sound or for the indication shown by a needle meter or by a digital meter, or for the intensity of light emitted by a displaying unit or by a light emitting diode (LED) or by several such LEDs. The adjustment may involve rotation of a knob or sliding a cursor along a ruler which reads the value of the unknown length. Guidance on the adjustment direction of the knob or cursor may be provided by following the pitch of the sound. Guidance on the adjustment direction may also be provided by the colour of a displaying device.

In a second aspect, there is provided a spectral interferometry apparatus using a broadband source and a linear array in a spectrometer which provides the measuring signal.

In a third aspect, there is provided a spectral interferometry apparatus where a tunable narrow band source and a photodetector unit delivers the measuring signal.

In a fourth aspect, measurement of the eye length is performed by focusing light on the anterior chamber of an eye, collecting light from the anterior chamber via a first optical delay and collecting light from the retina along a second optical delay, and where the measurement consists in adjusting one of the first or second delay or both until maximising the indication of a meter or the intensity of a light source or the strength of a sound of a certain frequency. Embodiments are disclosed based either on a large band source and a linear camera, or based on a tuneable narrow band source and a photodetecting unit.

In a fifth aspect, a configuration of Talbot bands is implemented to shift the maximum sensitivity of the FD-LCI method away from zero OPD, to a value of reference, $OPD_{ref}$ and where the measurement of the unknown length is concluded when the OPD is adjusted to $OPD_{ref}$.

In a sixth aspect, an interferometer configuration made from two interferometers in series (a tandem interferometer) is used, where the unknown length is part of the lengths of arms forming a $1^{st}$ interferometer (sensing interferometer, of optical path difference, $OPD_1$), a device is employed to modify an adjusting length, part of the optical path difference, $OPD_2$, in a $2^{nd}$ interferometer (adjusting or receiving interferometer) and a spectral interrogating unit outputs a measuring signal whose frequency is proportional to the difference of the $OPD_1$ and $OPD_2$, and where for example, the unknown length is the eye length.

In a seventh aspect, an interferometer configuration is employed made from two interferometers, and where for the OPD in each interferometer, $OPD_1$ and $OPD_2$, an output optical signal is produced by each interferometer and where a spectral interrogating unit processes both output optical signals to deliver an electric measuring signal to a nonlinear electronic amplifier followed by a low pass filter that provides an electric signal whose frequency is proportional to the difference of the $OPD_1$ and $OPD_2$, In an eighth aspect, an interferometer configuration is employed made from two independent interferometers, for the OPD in each interferometer a measuring signal is output by each interferometer and where for the OPD in each interferometer, $OPD_1$ and $OPD_2$, an output optical signal is produced by each interferometer and where a separate spectral interrogating unit processes each output optical signal to deliver each, an electric measuring signal, and where a two input electric mixer followed by a low pass filter is used to mix the two electric measuring signals to produce an electric signal whose frequency is proportional to the difference of the $OPD_1$ and $OPD_2$.

In a ninth aspect, a method and apparatus are provided to perform the operation of a stethoscope to produce sound at the rate of a heart beat.

In a tenth aspect, an analogue linearization solution is provided, for the frequency reading of signals from a linear CCD array or from a photodetector unit when using a swept source.

The novel features which are believed to be characteristic of the present invention, as to its structure, organization, use and method of operation, together with further objectives and advantages thereof, will be better understood from the following drawings in which presently preferred embodiments of the invention will now be illustrated by way of example.

It is expressly understood, however, that the drawings are for the purpose of illustration and description only and are not intended as a definition of the limits of the invention.

BRIEF DESCRIPTION OF THE DRAWINGS

Embodiments of this invention will now be described by way of example in association with the accompanying drawings in which.

Where optical fibres are used, this is only as an example and it should be noted that a bulk implementation is equally feasible, in which case the respective elements using in-fibre components, are to be replaced by optical paths and the directional fibre couplers by bulk beam-splitters, in the form of plates or cubes. Likewise, where bulk components are used, they could equally be replaced by optical fibre components.

DETAILED DESCRIPTION OF THE INVENTION

The novel features which are believed to be characteristic of the present invention, as to its structure, organization, use and method of operation, together with further objectives and advantages thereof, will be better understood from the following discussion.

Figure 1:
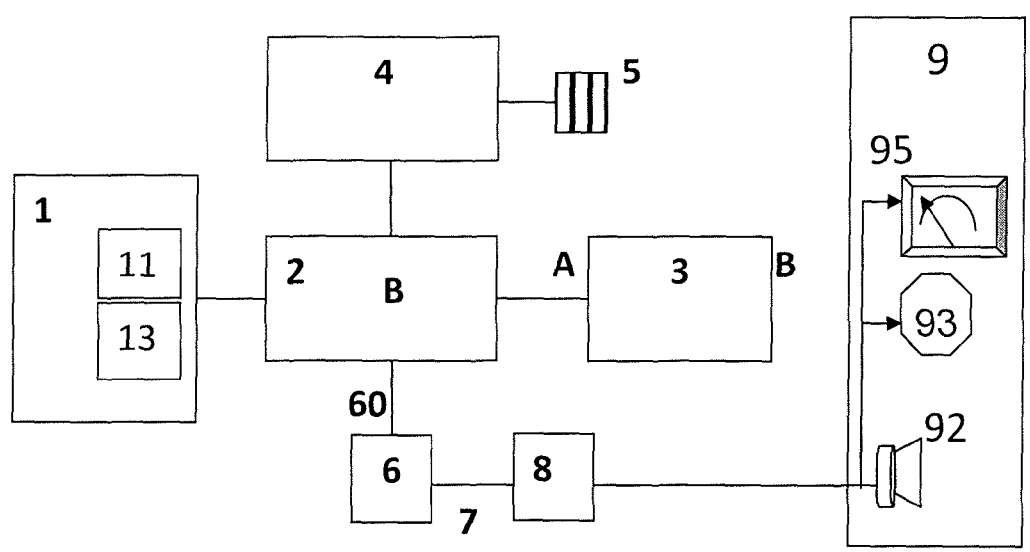
FIG. 1 shows a block diagram of an apparatus according to the invention.

An embodiment of the apparatus according to the invention is shown in block diagram in FIG. 1, where light from an optical source block 1 is sent to an interferometer configuration, 2. This may consist in a single or more interferometers. The OPD in each such interferometer is determined by the difference between a reference path length and an object path length. The object path length is measured from the interferometer configuration, up to a point, point A on the object 3. The reference path length can be measured either along a reference path length inside the interferometer configuration, or up to a point on the object, point B.

In the first case, the apparatus is used to measure distance AB between the object, 3 and the interferometer configuration, 2, in which case an arbitrary point B is considered inside the apparatus, shown for example inside block 2. In the second case, the apparatus is used to measure the thickness AB of the object 3. The OPD in each interferometer can be adjusted actuating on a translations stage, 4, equipped with measuring means, 5, in the form of a micrometer screw, a graded knob or a sliding ruler. Equivalently, the translation stage may be replaced by a spectral scanning delay line, using a diffraction grating, a focusing element and a tilting mirror according to means known in the art, and where the OPD is adjusted by tilting the mirror. The output optical signal, 60, is sent to a spectral interrogator, 6. The spectral interrogator may consist in a single or more spectral interrogating units, one for each output optical signal from each interferometer. Each spectral interrogating unit produces a measuring signal 7, and if more measuring signals are produced, then all are sent and processed by an electronics processing unit, 8. This may include bandpass filters, a mixer, or a nonlinear amplifier. Signals from different blocks inside 8, are delivered to indicators, in a block of indicators, 9. This contains at least a loudspeaker, or at least an earphone 92, outputting as indicating signal sound, or a displaying unit, equipped with an LED or several LEDs of different colours, 93, outputting as indicating signal light or a needle indicator 95, such as a voltmeter or ammeter, or a digital meter, outputting as indicating signal, a needle indication or a digital value. The optical source block includes a broadband optical source, 11, or could be a narrow band, tuneable source, SS, 13.

Figure 2:
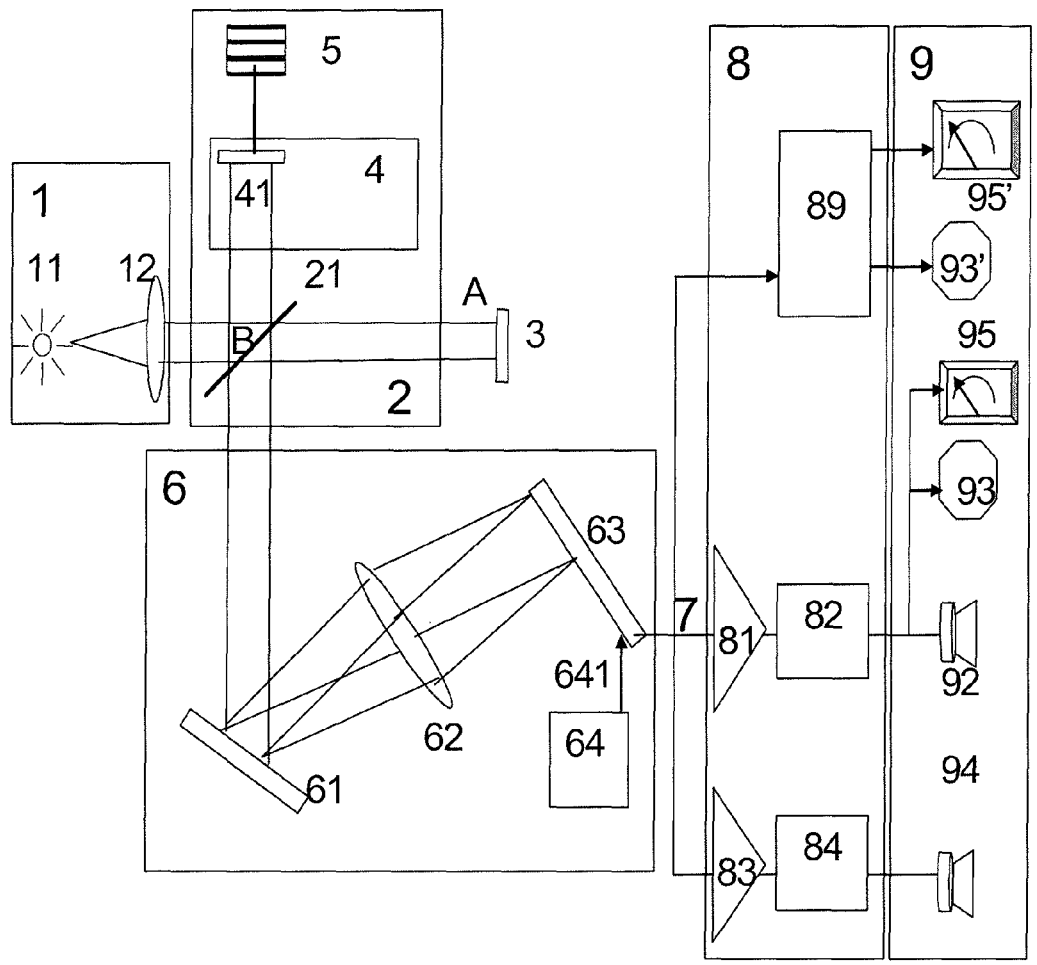
FIG. 2 shows a detailed embodiment of the invention using FD-LCI

FIG. 2 shows details of an embodiment of apparatus according to the invention, where the optical source 1 consists in a broadband source, 11 [such as a superluminiscent diode (SLD), a light emitting diode (LED), a thermal source, or any other optical source providing a wide linewidth, such as a photonic crystal fibre] and a collimating optical element, 12, in the form of a curved mirror or lens. The interferometer configuration consists in a single interferometer, equipped with a $1^{st}$ splitter, beamsplitter 21, which splits light into two arms, a reference arm towards a mirror 41 in the adjusting length device 4, and an object arm towards the $1^{st}$ point, A, on the object 3. Here distance is monitored or measured between point A, on object 3 and $1^{st}$ splitter, beamsplitter 21, where the 2nd point, B is considered virtually situated inside the apparatus. Here, the distance AB is measured from the object to the apparatus. Light beams returned from 3 and 41 are sent to the spectral interrogator, 6, which consists in a single spectral interrogating unit, made from a spectrometer employing dispersing element, 61, in the form of a prism or diffraction grating, a focusing lens in the form of a curved mirror or lens, 62, and a linear CCD or CMOS array, 63. Such devices have 512 to 4096 pixels, as an example only, and these pixels are read in sequence at a frequency F, as determined by the signal 641 delivered by a clock generator 64. The measuring signal 7 is sent towards the electronics processing unit, 8, which consists in one or more signal processing channels, two channels are shown for example only, equipped with amplifiers 81 and 83 and band pass filters 82 and 84, which drive the block of indicators 9, consisting in loudspeakers 92 and 94, display device 93 and/or voltmeter 95.

Figure 3A:
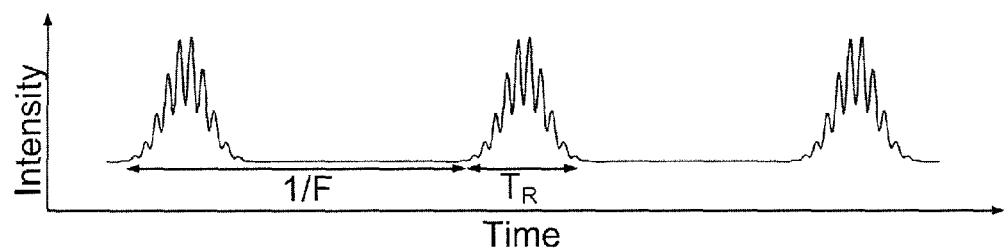
FIG. 3A displays the typical output of a linear camera in an FD-LCI based spectral interrogating unit showing repetitions in time of the channelled spectrum.
Figure 3B:
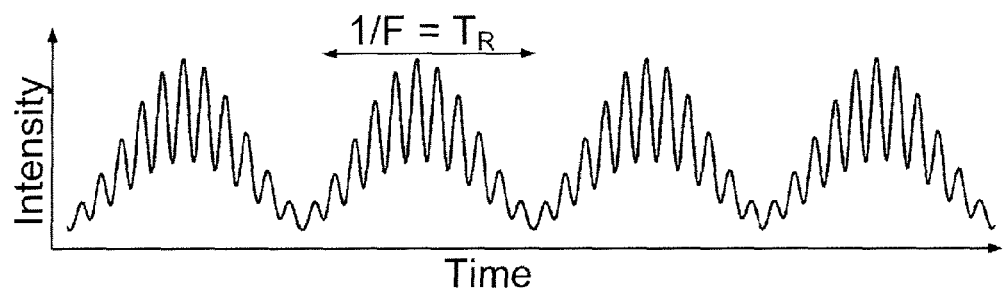
FIG. 3B displays the optimized output of the linear camera used to read the channelled spectrum.

The measuring signal 7 is fed out in a reading time $T_R$, which is less than 1/F usually, as shown in FIG. 3a. If such a signal is sent to a spectrum analyser, multiple components at frequencies F with side bands at $1/T_R$ are produced. According to the invention, for the application described here, it is important that the spectrum is as clean as much as possible, to allow provision of the useful information related to the OPD to be measured, deprived from stray frequency components. In order to clean the spectrum, the reading time, $T_R$, is adjusted to be as close as possible to 1/F. In this way, the signal output from the array looks like a smooth modulation with no interruption, as shown in FIG. 3b.

Figure 4:
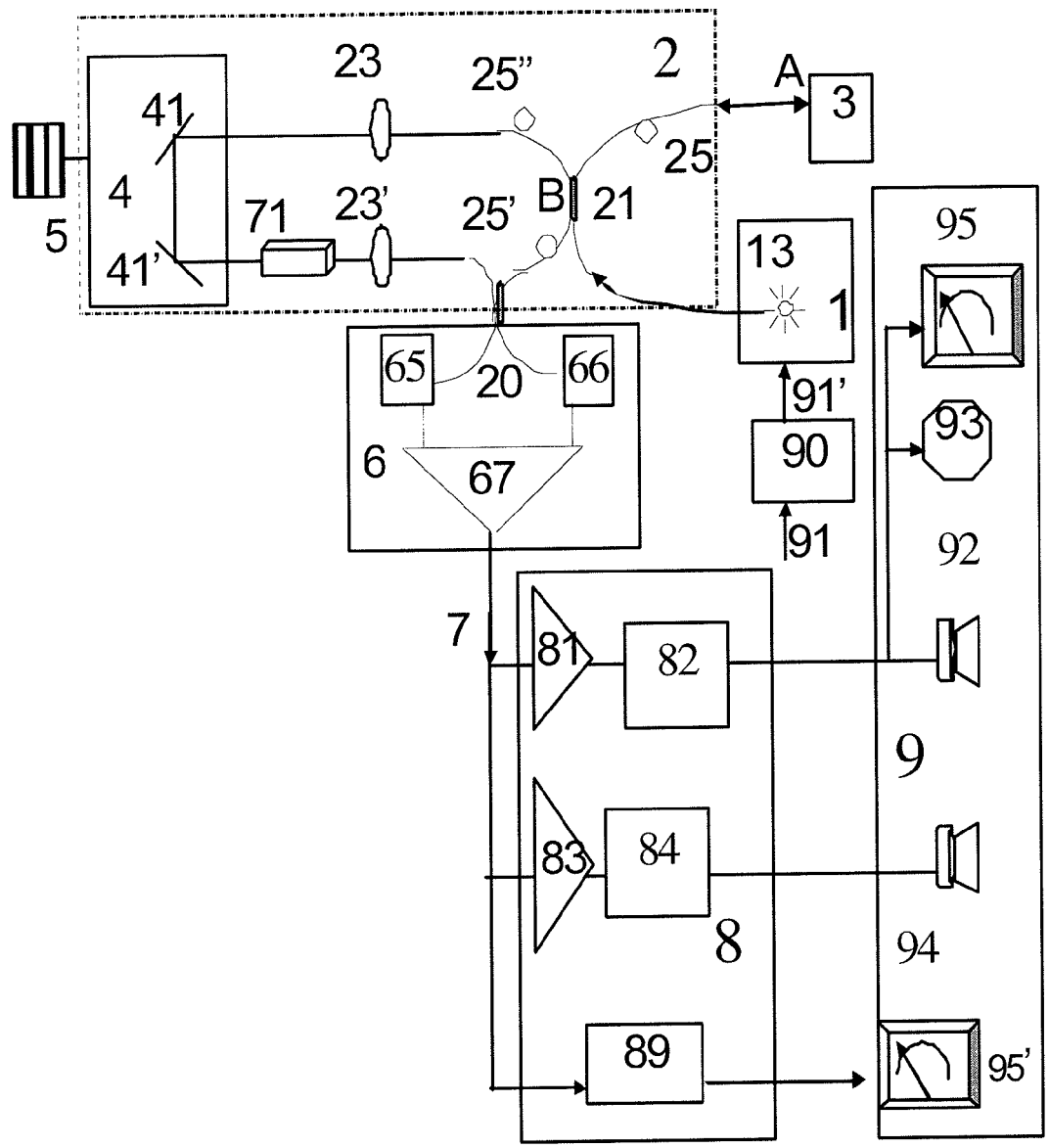
FIG. 4 shows a detailed embodiment of the invention using SS-LCI

FIG. 4 illustrates another embodiment of the invention where principles of SS-LCI are used. In this case, the optical source block, 1, is made of a tuneable narrow band source, 13.

Those skilled in the art will recognise that different configurations are now known for optical sources to provide fast tuning rates of more than 100 kHz, of linewidth less than 0.1 nm within a bandwidth of more than 50 nm. Such sources use ring lasers equipped with an optical amplifier and an optical filter, as described in the following papers: M. A. Choma, K. Hsu J. A. Izatt, "Swept source optical coherence tomography using an all-fiber 1300-nm ring laser source," *J Biomedical Optics* 10_4, 044009_pp. 044009-1 to 044009-6, 2005 and R. Huber, M. Wojtkowski, and J. G. Fujimoto, "Fourier Domain Mode Locking (FDML): A new laser operating regime and applications for optical coherence tomography," *Opt. Express* 14, pp. 3225-3237, 2006.

However, such sources are still very expensive and it is not generally desirable to pair a low cost optical configuration as presented in this disclosure with such expensive sources. For the purpose of the invention, lower cost sources are therefore preferred, such sources may be based on a semiconductor laser diode whose current is ramped. Such sources are known in the field of frequency modulation continuous wave (FMCW) sensing, as for instance used in the article "Reflectometric fiber optic frequency-modulated continuous-wave interferometric displacement sensor" published by Zheng, J in Optical Engineering, Vol. 44, Issue 12, Article Number: 124404, December 2005 In this way, a few nm tuning bandwidth is easily achievable. The small tuning bandwidth leads to a poor depth resolution. However, even depth resolutions worse than 50 microns could be tolerated for certain measurements in low cost solutions. Other low cost swept sources are being developed which could find applications in the invention, using micro-electro-mechanical (MEM) based tuneable resonators. The larger the tuning bandwidth the higher the cost of such sources. For digital processing, a Fabry-Perot interferometer is usually incorporated into a swept source to provide a clock which is subsequently used for linearization of data. If tuning bandwidths of 5-10 nm are targeted, then the swept source is further simplified and its cost is dramatically reduced by not including any clock generation and no other circuit for linearization.

The spectral interrogator 6 in FIG. 4 uses a single spectral interrogating unit made from a photodetection unit equipped with a single photodetector or preferably, two photodetectors, 65 and 66 in a balanced detection configuration with a differential amplifier 67 that produces the difference of the two photodetected signals and delivers the measuring signal 7. This is then sent to the electronics processing unit 8. An in-fiber configuration is shown in FIG. 4, used to implement a single interferometer in the interferometer configuration 2. Light from the swept source, 13, is sent to a splitter, 21, implemented here as an example using a single mode directional coupler which splits light into the object arm towards the point A, on the surface of object 3 and into the reference arm, towards mirrors 41 and 41' placed on the translation stage 4, using focusing elements 23 and 23'. Light from the object 3 is returned via 21 towards a balanced splitter, 20, implemented here as an example using a single mode directional coupler, where it interferes with light from the reference arm. The interferometer is equipped with means known in the art to optimise the polarisation orientation for maximum interference, such as polarisers 25, 25' and 25" and equipped with means to compensate for dispersion, such as optical slabs, 71.

Procedure

For both embodiments in FIGS. 2 and 4, a band pass filter, 82 is set on a frequency corresponding to a desired reference OPD value. For a central wavelength □, spectral width □□, the axial range, from point A to point B is given by □Z=0.25M □□□□ where M are the number of pixels in the CCD array in FIG. 2 or the number of resolvable frequency steps for the SS in FIG. $\tilde{4}$. For a central wavelength of 800 nm, the equivalent coherence length for a source with Gaussian spectrum is $l_c$=0.44 □□□□, this characterizes the depth resolution, i.e. the differential distance between adjacent sampling point values on the horizontal axis of the FFT. By equivalent coherence length $l_c$ we mean here the coherence length of an equivalent time domain (TD)-LCI system excited by a broadband optical source 11 in FIG. 2 with spectrum width □□ equal to the tuning bandwidth □□ of the source 13 in FIG. 4. For example, for a □□□□̃ nm, $l_c$ □̃□□ m. The ratio □Z by $l_c$ determines approximately the number of modulating cycles in the channelled spectrum, 0.25M/044~M/2. For an OPD=$l_c$, the channelled spectrum exhibits one spectral modulation period and M=2 pixels are needed at least in the linear array 63 in FIG. 2 or at least M=2 frequency steps are required in the process of tuning the SS, 13, in FIG. 4.

Let us say that we choose to identify an unknown OPD=□Z, as a small part of the distance between the surface of the object 3, point A, up to the interferometer, point B. This would mean a □Z/$l_c$ number of cycles in the channelled spectrum. Reading the linear array 63 in FIG. 2 at a frequency F, or tuning the frequency of the source 13 in FIG. 4 at a frequency F, will output a measuring signal, 7, of frequency f=F(□Z/$l_c$).

The Audio Signal can be Utilised in Two Ways:

Intensity

A band pass filter, 82, will only transfer signal to its output when the frequency of the input signal is within its bandwidth, therefore the central frequency of the band pass filter defines a reference frequency that can be chosen in the process of monitoring or measurement. This reference frequency corresponds to a chosen reference OPD value, $OPD_{ref}$. Let us consider a readout CCD (or tuning) frequency F=1 kHz and $OPD_{ref}/l_c$=10. This corresponds to a chosen reference value of the audio frequency $f_{ref}$=10 kHz, as the main component in the frequency spectrum of the measuring signal. The measuring means 5 in FIG. 2 and FIG. 4 are adjusted to obtain a maximum for the signal strength at frequency $f_{ref}$ in loudspeaker 92. The narrower the band of the band pass filter 82, the better the accuracy in the axial measurement. The maximum of sound heard in the loudspeaker 92 will indicate that the length of the OPD has reached the sought after reference value $OPD_{ref}$ and an indication of that length will be given by 5.

Pitch

Seeking maximum intensity in the loudspeaker requires scanning a knob or sliding a ruler in 5 in both directions. Preferably, the invention uses both the intensity of the signal at the output of 82 tuned on $f_{ref}$ as well as the pitch of the sound. To this goal, a second large bandwidth band pass filter, 84 is used. The pitch gives an indication on the direction of adjusting the measurement means 5. For the example above, the band pass filter 84 allows audio frequency signals of frequency 1 to 18 kHz, within the human hearing band.

The relative amplitude of the two signals in the two loudspeakers can be controlled by relatively adjusting the amplification in the amplifiers 81 and 83. When the signal entered into the bandwidth of 82, the signal in the loudspeaker 94 can be reduced to zero and the measurement finalised by maximising the sound in 92. Alternatively, only one loudspeaker is used, 94, to provide information on the direction of rotating the knob or sliding the cursor 5, and the optimum adjustment will only be guided by producing maximum in the light display device or LED 93 or/and the voltmeter 95. As a further possibility, several coloured LEDs are used, with different threshold actuating levels. A liquid crystal display device may also be used, or a coloured display device that displays stripes of coloured bands, where the frequency of the colour is proportional to the amplitude of the signal. Several possibilities exist to sensitize the measurement, known being that the eye is more sensitive to colour difference than to the colour itself. Therefore, for each new position of the measuring means 5, the display device 93 provides at the same time, stripes of colour corresponding to the previous OPD value as to the current OPD value. The colour difference will then suggest the direction of adjusting the OPD using 5.

It is also possible to convert the frequency of the reading signal 7, into amplitude directly, using a frequency to amplitude convertor, 89, that drives a needle instrument, 95', or a digital meter, 93'.

The measurement of OPD in both cases above relies on the value shown by the calibrated knob 5. This could be a micrometer screw, with divisions at 10 microns. Interpolation between such divisions can give a resolution in measurement better than 5 microns.

Figure 5:
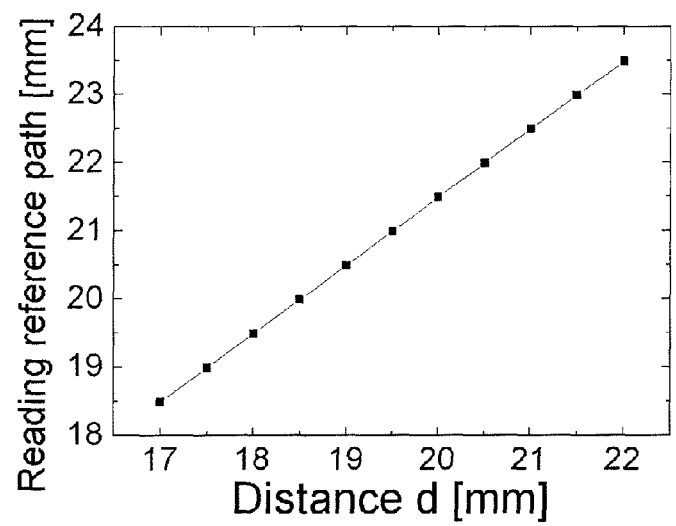
FIG. 5 shows the plot of length measurements of a varying length following the strength of sound in the embodiment in FIG. 2.

A proof of concept was set-up for the embodiment in FIG. 2 using a band pass filter 82 tuned on 2.7 kHz with a bandwidth of 67.5 Hz. A mirror was used as an object, 3, placed on a stage whose distance was changed in steps of 0.5 mm. Then, by using the micrometer screw 5, the OPD was adjusted until maximum signal strength was obtained in the loudspeaker 92. The position was read on the scale of the micrometer screw 5 and the graph in FIG. 5 was obtained. This shows that by simply following the sound in a loudspeaker and using a ruler, the distance from object 3 up to the interferometer can be measured and monitored with better than 10 micrometer accuracy.

Applications

The method according to the invention can be used for measurement as well as to monitoring of distances. The stage 4 can be set at a reference value and from that moment, the fluctuation in distance of the object mirror 3 can be evaluated by moving stage 4 until sound is regained in the loudspeaker 92. Automatic procedures can also be devised according to means known in the art, by using the signal towards loudspeaker 94. If the pitch sound is higher than the desired frequency $f_{ref}$, by actuating on means 5, the stage 4 is moved in the direction of increasing the reference path, to reduce the OPD=object path−reference path. If the pitch is lower than $f_{ref}$, then the stage 4 is moved to reduce the reference path length in the interferometer, and so on.

Eye Length Measurement

Figure 6:
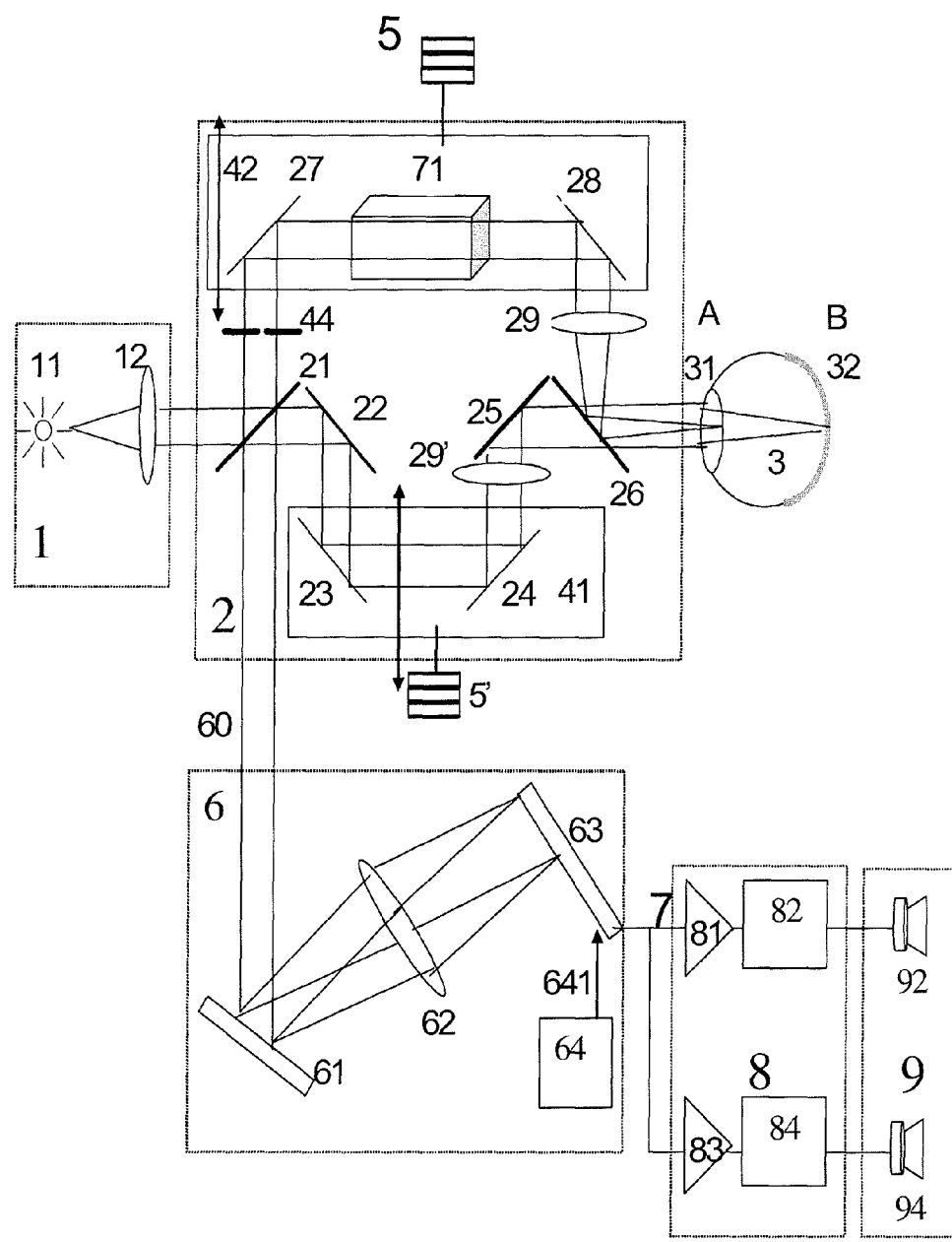
FIG. 6 displays a first version of an apparatus for measuring the eye length using FD-LCI according to the invention.

FIG. 6 illustrates an FD-LCI embodiment for the spectral interrogating unit where the eye length of a patient, the distance between point A, on the cornea and point B, on the retina, is measured using the method according to the invention, based on sound monitoring or a meter indication or light produced. The output beam from the optical source, 1, is split into two beams by splitter, 21. The first beam, object beam, is reflected towards mirrors 27 and 28 placed on a translation stage 42, whose position is adjustable via the micrometer screw 5, part of measuring means, and then focused via an interface optics, shown in the form of a lens 29 and a splitter, 26 on the cornea 31 of the eye 3. The second beam, reference beam, is sent to the retina, 32, of an eye, 3, via mirror 22, 23, 24, 25 and splitter 26. The mirrors 23 and 24 are placed on a translation stage, 41, which can be adjusted by micrometer screw 5'. To focus light on the retina, 32, the reference beam needs to be collimated for emmetropic eyes. For long sighted or short sighted eyes, a reference interface optics may be used to axially modify the focus position on the retina of the reference beam. A converging or diverging lens 29' or a curved mirror, or an electrically controlled liquid crystal lens, or a deformable MEM mirror can be used as 29 and 29'.

A channelled spectrum is created by the interference of the two beams, object and reference reflected of the cornea 31, point A and from respectively retina 32, point B. The cornea signal is at least 1000 time stronger than the signal from the retina. Therefore, in order to balance the strengths of the two reflected signals, splitter 26 has a transmission much higher than its reflection, for instance 95% transmission (in which case a simple glass plate antireflection coated on one side could be used, or even 99%). Additional correction of amplitudes can be obtained by adjusting the transmission of the splitter 21 to larger values than its reflection, in order to maximise the signal from the retina 32 for an input power towards the eye close to the safety limit. Further, an adjustable pinhole, 44, can be used to reduce the power towards the top, 31, of the object 3. In case the object is the eye, this also helps with extending the depth of focus of the object beam, to make the apparatus compatible with non-accurate axial distance position of the object 3 in respect to the apparatus.

One or both of the micrometer screws 5 or 5' parts of the measuring means can be calibrated. The audio frequency of choice, $f_{ref}$, can be chosen in the range 0.5-15 kHz to correspond to a certain OPD value of reference, $OPD_{ref}$. This could be associated to the minimum, or the maximum, or the middle value in the range of eye lengths, let us say, to a value E=23 mm between points A and B. To accommodate measurements of eyes shorter or longer than this value, the micrometers 5 (or 5') are equipped with rulers graded from 17 to 29 mm. Adjusting 5 or 5' to regain maximum strength in 92 guided by the pitch in 94 leads to the current eye length value, E. Obviously, because the linear photodetector array, 63, may have only 1000-2000 pixels, the axial range may be limited to 1 to 4 mm. Therefore, the procedure involves turning the knob of the calibrated micrometer screw 5, or 5' or both until sound is heard in 94 followed by enhancement of sound in 92. It is possible that position of knobs (cursors, micrometer screws) 5 and 5' are such that the OPD value is out of the limited axial range. In this case, the adjusting knob 5 or 5' is moved to one extremity and back until the highest pitch, 18 kHz is heard. From that moment, adjustment is made to bring the pitch of the sound to that corresponding to the reference value □z.

The embodiment in FIG. 6 can also operate as a tandem interferometer, according to the sixth aspect of the invention. In this case, the $2^{nd}$ interferometer is constructed as a reading interferometer, operating in tandem with the sensing interferometer formed between interfaces 31 and 32. In this case, lenses 29 and 29' are such as they allow signals from both interfaces 31 and 32 being transferred to each of the paths of the sensing interferometer, one along 26, 28, 27, 21 and the other along 26, 25, 24, 23, 22 and 21.

Figure 7:
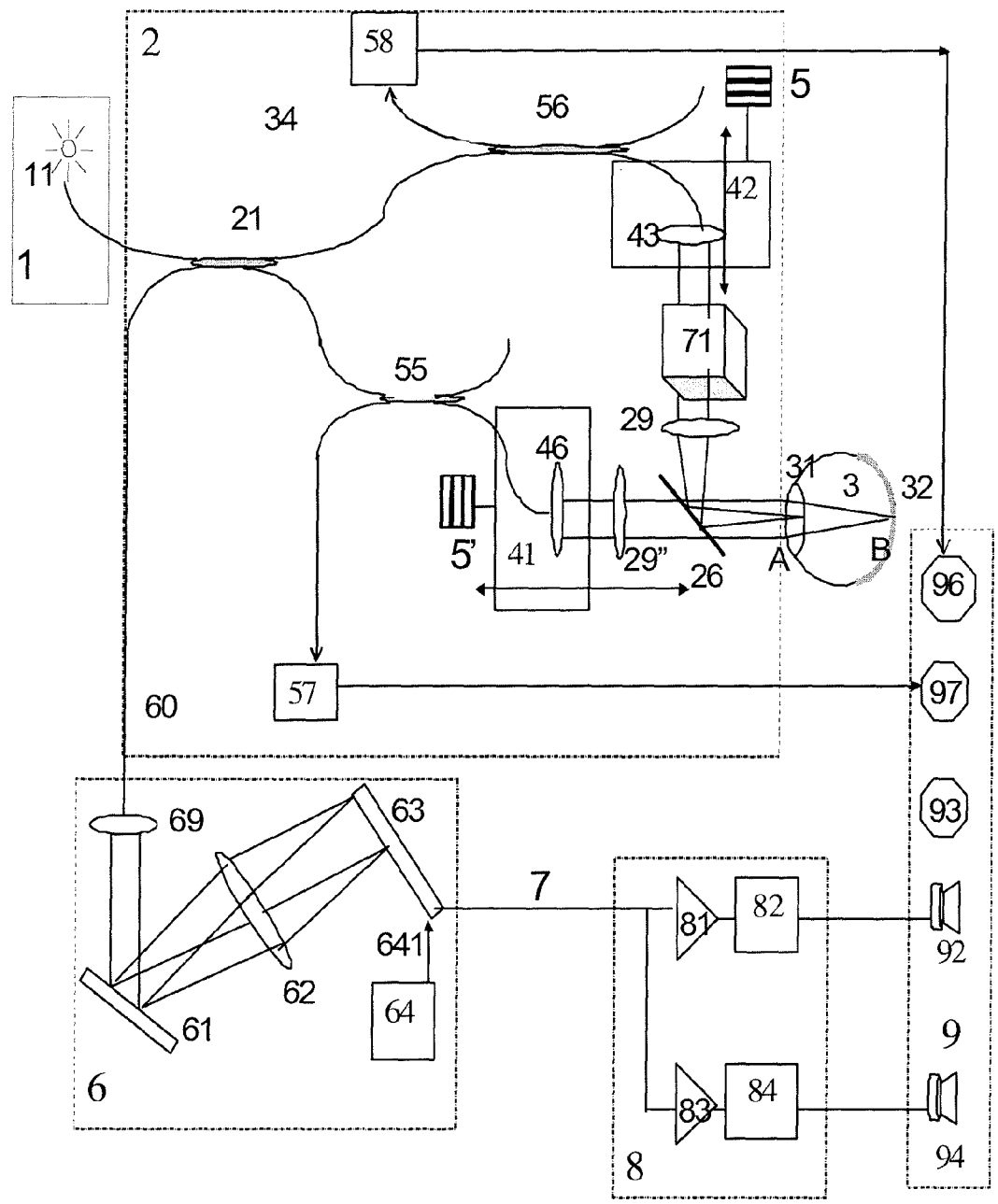
FIG. 7 exemplifies a second version of an apparatus for measuring the eye length using FD-LCI according to the invention.

FIG. 7 shows an equivalent of the embodiment in FIG. 6, where the optical splitter, 21, is a single mode directional coupler. The fiber output of 21 connects to the launchers situated on stages 41 and 42, via two couplers, 55 and 56 respectively. The positions of stages 41 and 42 are adjusted to bring the optical path difference between the object path towards the cornea 31 and the reference path towards the retina, 32 to the reference value, $OPD_{ref}$ which determines the sought after strength and pitch, $f_{ref}$ respectively in the loudspeakers 92 and 94. The two beams, object from point A, on the cornea 31 and reference beam from point B, on the retina, 32, are handled separately, as light form retina does not go through lens 43 and light from cornea does not go through lens 46. The object interface optics is formed from lenses 43 and 29 and aims to focus light on the cornea, 31. Lens 46 is adjusted to send a collimated beam towards the eye 3, in case the eye is emmetropic. For a short sighted or long sighted eye, the lens 46 can be moved in relation to the output fiber of splitter 55, to adjust the convergence of the reference beam launched into the eye 3, the fiber end and lens 46 are identified as parts of the reference interface optics. The output of coupler 21 provides the output optical signal 60, whose channelled spectrum is to be interrogated by the spectral interrogator 6 using a single interrogating unit, based on a spectrometer. Optical signal 60 is launched as a collimated beam, via focusing element 69, towards the diffraction grating 61.

To tolerate eventual placements of the eye 3 away from the ideal axial position where the object beam focuses on the cornea 31, lens 43 has a small focal length to prepare a small diameter beam launched towards the lens 29, and lens 29 has a long focal length, and in this way, a long depth of focus is achieved. This advantageously leads to less efficiency in collecting backscattered light from the cornea, 31, than from the retina, 32.

As additional elements which can be carried to the other embodiments dealing with eye length measurement, two indicators, 96 and 97 are used in the indicating block 9, to inform the user that sufficient signal is returned from the point A on the cornea, 31 and from the point B, on the retina, 32. They could be LEDs, driven by photodetectors 57 and 58 respectively, at the output of single mode couplers 55 and 56 respectively. The two couplers 55 and 56 are used to tap small portions of the signals returned from retina and cornea to excite the photodetectors 57 and 58. Before any measurement, it may be necessary to adjust the convergence or divergence of the object and reference beams to enhance the strengths of the signals reflected from points A, 31 and B, 32. The adjustment can be performed by moving axially the lenses 29, 29', 43 and 46, or by using liquid crystal, electrically controlled lenses 29, 29', 43 and 46, or using deformable MEMS mirrors as 29, 29', 43 and 46. It may also be possible that converging elements, 29 and 29' are not inserted at all and adjustments are made using converging elements 43 and 46 only.

The process of measurement starts only if LEDs 96 and 97 are lit up. When 96 and 97 indicate sufficient strength, the measurement is initiated and consists in actuating on the adjusting means 5 and 5'. The object 3, a slab or the eye, is adjusted laterally until sufficient signal is returned to the interferometer configuration 2 from both A and B points. Only then the OPD is adjusted to achieve the pitch sought after, $f_{ref}$ in both loudspeakers 92 and 94 and maximum sound in loudspeaker 92.

Figure 8:
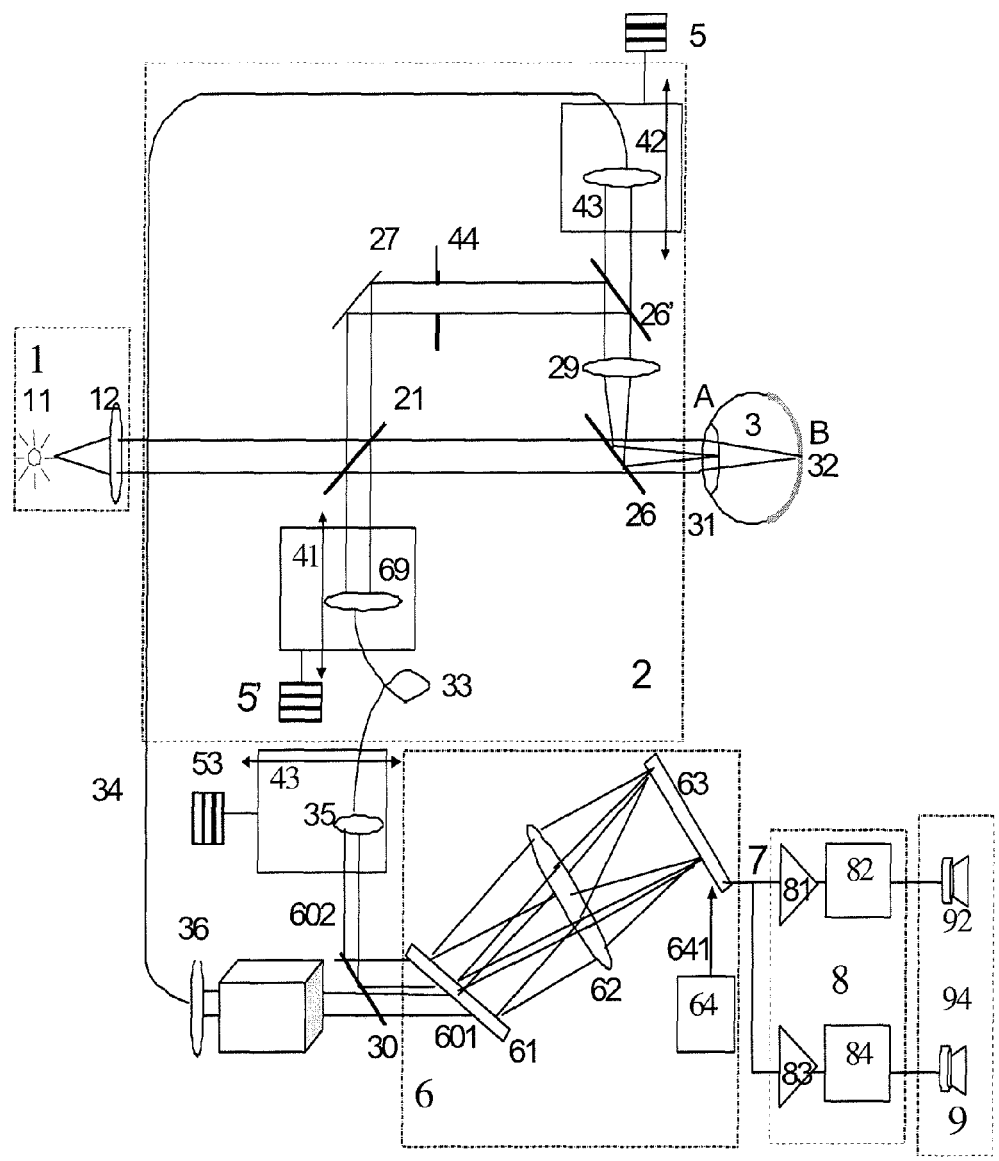
FIG. 8 exemplifies a third version of an apparatus for measuring the eye length using FD-LCI according to the invention.

FIG. 8 shows another embodiment, based on Talbot bands, where the two beams from the anterior chamber and from the retina are sent along separate paths towards the spectral interrogator unit, 6, using a single spectral interrogating unit equipped with a grating based spectrometer. Light coming from the splitter, 21, is deflected by a mirror 27, non-essential, towards the point A, on the surface of the cornea 31, via a splitter, 26 and splitter 26'. Light from cornea, point A, is split by splitters, 26 and 26', into the fiber launcher on stage 42 equipped with focusing element 43, focusing light into fiber 34. This carries the light from the point A, on the cornea of eye 3, or from the anterior chamber towards lens 36 which launches a collimated beam, 601, towards the grating 61, via optical splitter 30.

The light reflected from point B, the retina 32, traverses the optical splitters 26 and 21 towards the focusing element 69 in the fiber launcher placed on the stage 41, where light is launched into fiber 33. The two beams are separated, as light form point B, retina 32, does not go into fibre 34 and light from point A, cornea 31, does not go into fiber 33. Light from fiber 33 is then conveyed via focusing element 35 into a collimated beam, 602, via splitter, 30. The collimated beams 601 and 602 can be superposed or totally separated spatially by a gap using the translation stage 43 which moves the launcher with fiber end of fiber 33 and focusing element 35 laterally, using the micrometer screw 53, as explained in the US patent application 2007/0165234, Spectral interferometry method and apparatus, by A. Podoleanu.

Fibers 33 and 34 have similar lengths to keep the dispersion low, along with the element 71, which compensates for the dispersion in the eye, usually a cuvette of approximate length equal to twice the eye length and filled with water. The procedure of measuring the eye length is similar to that described above where one of the stages 41, or 42 or both are driven by micrometer screws 5 and 5'. The path difference in air between the two beams from the anterior and posterior chamber of the eye are adjustable using the two stages 41 and 42. One of the micrometer screws (or both) is (are) equipped with a ruler showing eye lengths of 17-28 mm, to cover the normal range of eye length values.

The advantage of the Talbot bands configuration is that the maximum sensitivity of the FD-LCI method can be shifted from OPD=0 to a larger OPD value. The sensitivity peak can be shifted to the value of OPD chosen as reference, $OPD_{ref}$, and that which gives the pitch of reference, $f_{ref}$ in the loudspeakers 92 and 94. The shift of peak of sensitivity from OPD=0 is proportional to the gap between the two beam 601 and 602 which can be adjusted using knob 53 to move stage 43 that displaces the beam 602 parallel to beam 601 in its way towards diffraction grating 61.

Figure 9:
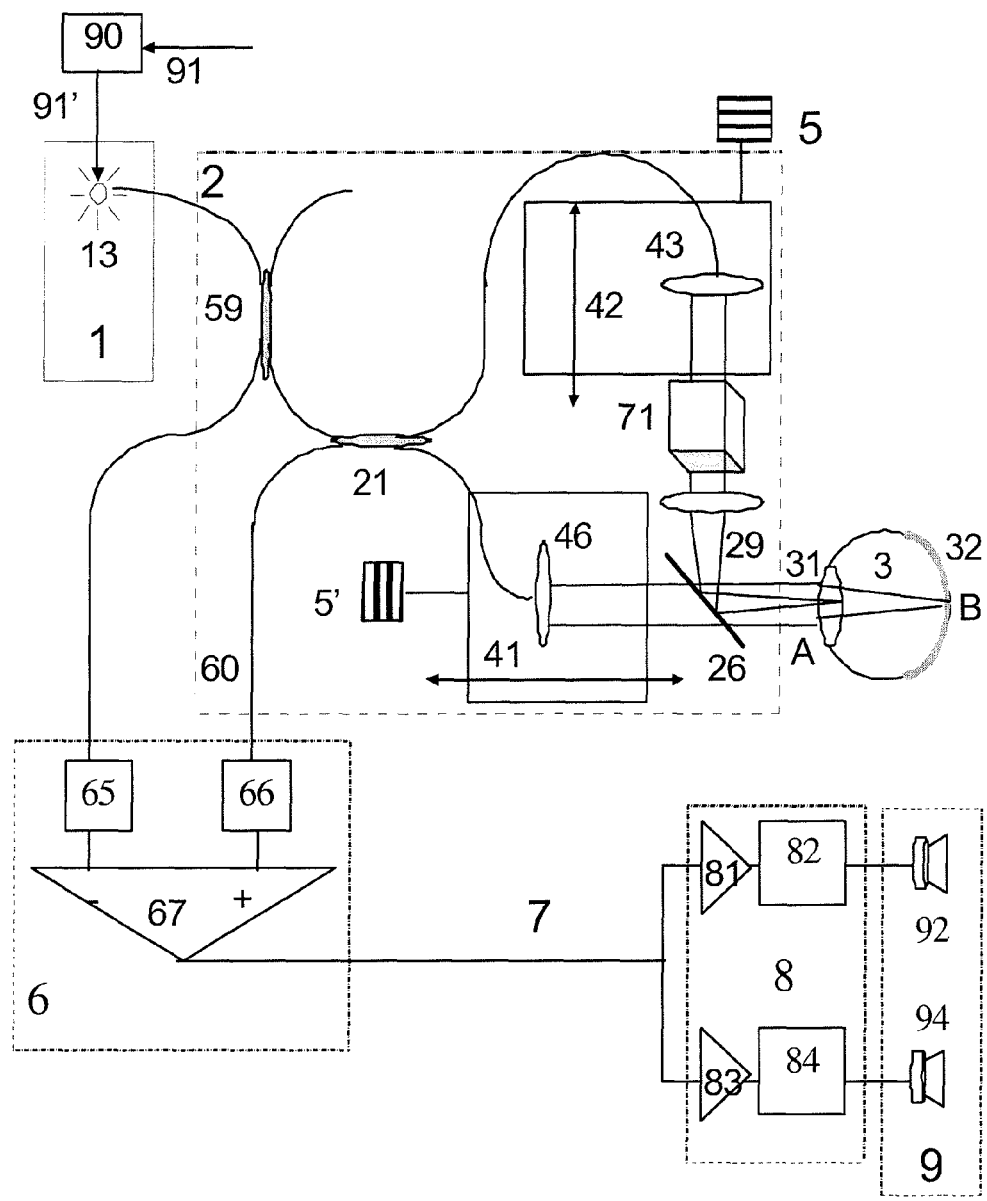
FIG. 9 shows an apparatus for measuring the eye length using SS-LCI according to the invention.

FIG. 9 discloses another embodiment for measuring the thickness of object 3 or eye length of an eye 3, where the optical source 13 is tuneable and narrow band. The interferometer configuration uses a single interferometer collecting light via separate paths from 31 and from 32. The spectral interrogator 6 uses a single spectral interrogating unit using photodetection. Balance detection is implemented using two directional couplers 21, and 59, feeding two photodetectors, 65 and 66 whose photodetection currents are deducted in the differential amplifier 67. The two beams, object, from point A on the surface of object 3, i.e. from cornea, 31, of an eye, and the reference beam from point B, retina, 32, are sent via separate paths. Light form retina does not go into the fiber aperture behind the focusing element 43 and light form cornea does not go into the fiber aperture behind the focusing element 46. The source 13 is tuned at a rate of 100 Hz for instance and for a reference optical path difference corresponding to 10 peaks in the channelled spectrum, the interference signal leads to an audio signal of 1 kHz.

Figure 10:
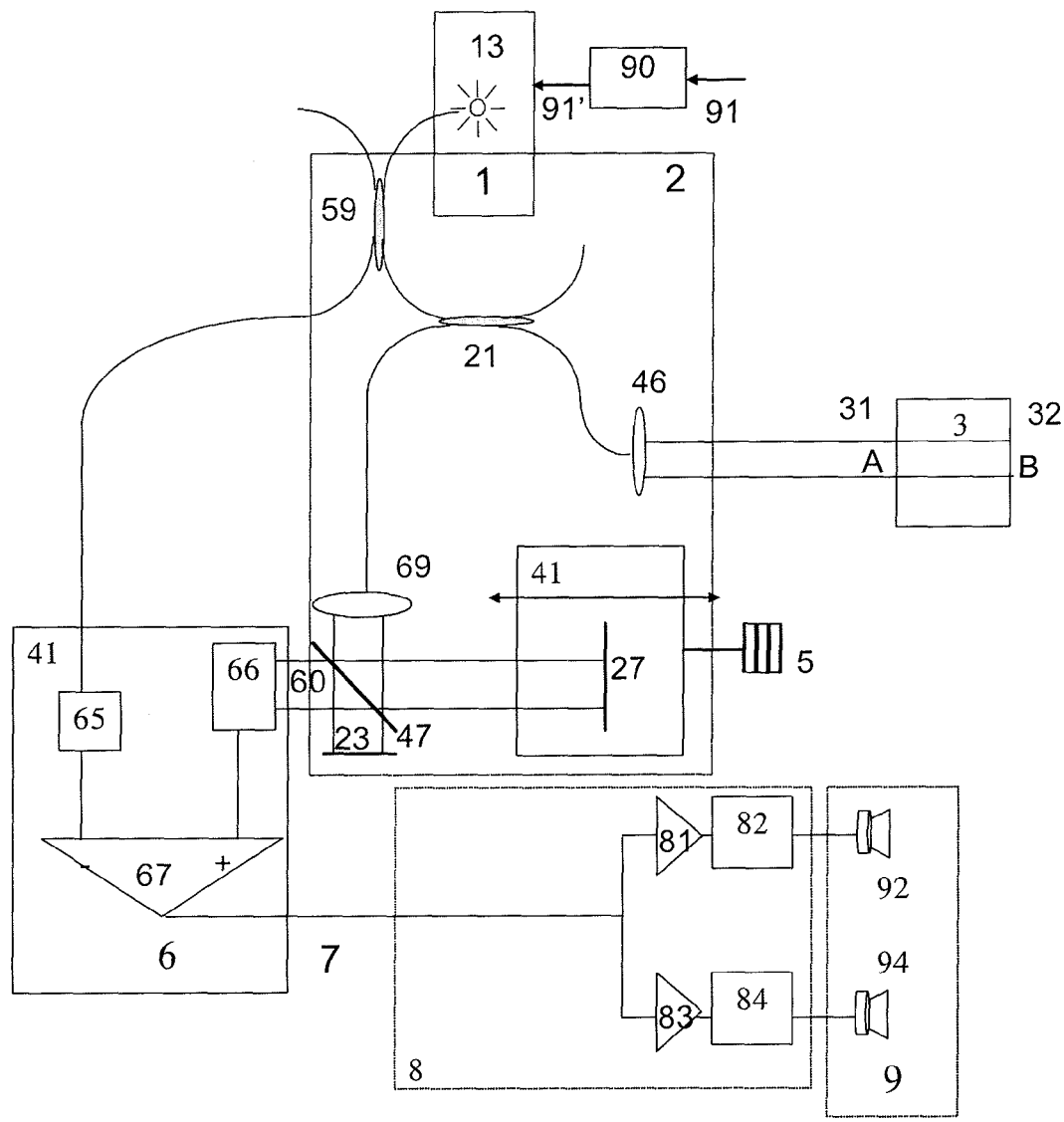
FIG. 10 shows an apparatus for measuring the thickness of an object using a common path probe head in a tandem interferometer configuration with SS-LCI interrogation according to the invention.

FIG. 10 discloses an embodiment where the thickness of the object, 3, a glass or polymer plate for instance subject to an external factor, is monitored using an interferometer configuration employing a tandem interferometer configuration. A first interferometer, sensing interferometer, is formed by reflections from the point A on surface 31, and from point B on surface 32 of the object 3, determining an $OPD_1$, and a second interferometer (a reading interferometer), which is adjustable in its optical path difference, $OPD_2$, is formed using splitter, 47 and mirrors 23 and 27. $1^{st}$ and 2nd interferometers are connected in series. Both $OPD_1$ and $OPD_2$ are much larger than the maximum range measurable, for instance over 1 cm, while the maximum range measurable is a few mm, axial range limited by the linewidth of the swept source. In such situations, the channelled spectrum is much denser than the instrument can decipher. Therefore, only when the difference $\square = |OPD_1 - OPD_2|$ enters within the axial range limited by the optical source linewidth, a resolvable channelled spectrum is produced. Using a configuration of tandem interferometry, the pitch of the signal 7 is determined by the value of $\square$. For each interferometer, a channelled spectrum modulation is produced. Let us say that the $1^{st}$ interferometer, of $OPD_1$ would lead to a measuring signal 7 which should pulsate at a frequency $f_1$ when tuning the source 13. The adjustable interferometer, of $OPD_2$ would determine a measuring signal 7 of frequency $f_2$ when tuning source 13. However, for large thickness objects 3, when the distance AB is larger than 1 cm, $f_1$ and $f_2$ cannot be measured due to the limited resolution conferred by the optical source linewidth. What can be measured, is the difference of such frequencies, corresponding to $\square$ onlỹ

Using the knob 5 to alter $OPD_2$, the difference $|OPD_1-OPD_2|$ is modified and consequently, the difference of frequencies $|f_1-f_2|$. Let us say that the source 13 is tuned at a rate F=100 Hz and the channelled spectrum corresponding to ☐ consists in 10 peaks. This means that a signal of frequency f=1 kHz is generated when $|OPD_1-OPD_2|=OPD_{ref}$. By adjusting the knob 5 to re-obtain the same pitch of 1 kHz in 92 and 94 allows monitoring of the $OPD_1$, value read from the calibrated ruler of knob 5.

Figure 11:
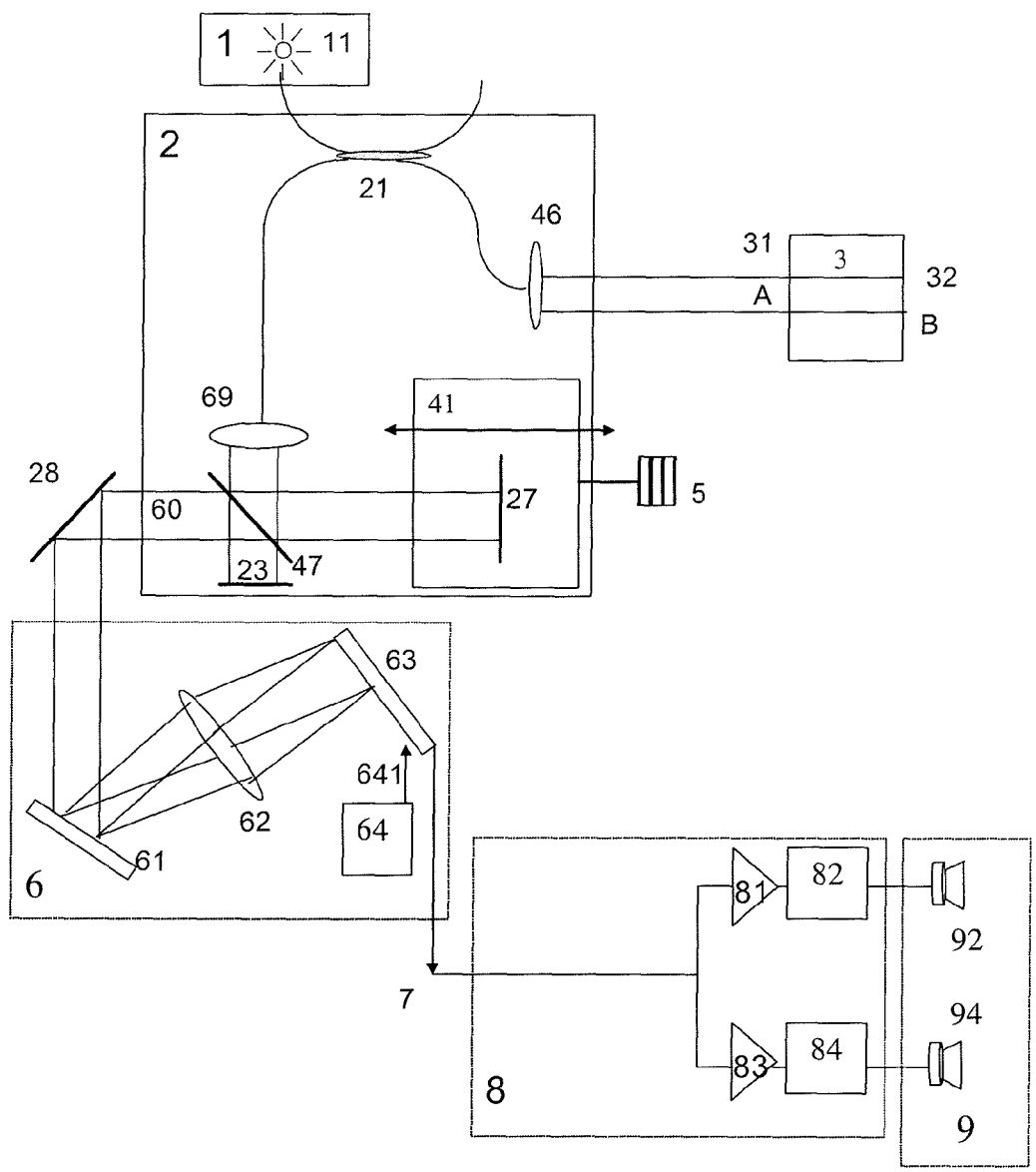
FIG. 11 shows an apparatus for measuring the thickness of an object using a common path probe head in a tandem interferometer configuration with FD-LCI interrogation according to the invention.

FIG. 11 discloses an equivalent embodiment to that shown in FIG. 10, this time using a broadband source, 11, and a spectral interrogating unit in the spectral interrogator employing the principle of FD-LCI. A tandem interferometer in the interferometer configuration is used as in FIG. 10. The measuring signal 7 is now delivered by the linear array, 63, with the repetition F in scanning the channelled spectrum, determined by the inverse of the integration time of the CMOS or CCD array used.

It should be obvious for the person skilled in the art that the succession of the two interferometers can be reverted in FIGS. 10 and 11, where light from the optical sources, 11 or 13, is sent first to the measuring interferometer, of $OPD_2$, and light returned from this interferometer is sent to the sensing interferometer, of $OPD_1$ (i.e. to the object 3). This can be simply achieved by reconfiguring the orders of splitters 21 and 47, to send light first to splitter 47 and then to object 3.

The tandem interferometry method used by embodiments in FIGS. 10 and 11 rely on both signals from A and B being returned to the same fiber aperture with sufficient strength, as practised in common path LCI and OCT. The length of fiber between the splitter 21 and focusing element 46 does not influence the $OPD_1$, this is a common path transferring optical signals from both interfaces 31 (A) and 32 (B). The focusing element 46 determines a long depth of focus allowing sufficient strength signal from both points, 31 and 32. For better efficiency, in both FIGS. 10 and 11, all elements of block 2 from FIG. 6 can be employed around splitter 21 to deliver light to the eye 3, with output of splitter 21 delivered to splitter 47.

The tandem interferometry embodiments in FIGS. 10 and 11 implement a regime that leads directly to the difference of frequencies $f_1$ and $f_2$ in the spectrum of the measuring signal 7. This difference can also be created using a two beam interferometer scheme, as disclosed in FIG. 12. In the embodiments in FIGS. 10 and 11, interference was produced between the two measuring points, and often, the interfaces from the object return low level signals and the resulting interference signal is therefore weak. To improve on the signal strength, the embodiment in FIG. 12 operates on a different principle, where the interferometer configuration consists in two interferometers, each sending its own output signal towards the spectral interrogator unit 6. A first output optical signal is created between object signal from point A (of low strength) and a local reference signal, A' of high strength. The optical path difference between A and A' is $OPD_1$ and the frequency generated by reading the channelled spectrum due to interference of signals from A and A' is $f_1$. A second output optical signal is produced between object signal returned from point B (of low strength) and a local reference signal, B', of high strength. The optical path difference between B and B' is $OPD_2$ and the frequency generated by reading the channelled spectrum is $f_2$. The spectral interrogator 6 outputs a measuring signal containing in its spectrum both frequencies $f_1$ and $f_2$. Then, electrical mixing in 85 leads to the difference of frequencies.

To achieve such functionality, light from source 11 is split by splitter 45, light at its $1^{st}$ output is directed via interface optics towards the two points, A and B. At the $2^{nd}$ output, light is sent to splitter 37, which splits light towards mirror 38 (point A') and mirror 39 (point B'). Let us say that the length along 21, 27, 28, 26 up to 31 (A) is similar to that along 21, 22, 23, 24, 25, 26 and 32 (point B). Then the distance between 37 and 38 is longer than the distance between 37 and 39 by the eye length (or the thickness to be measured, AB=E). It is recommendable that frequencies $f_1$ and $f_2$ are larger than the audible range. Let us say that AA' fluctuates due to the axial (eye) movements, determining a variation in the channelled spectrum from 10 to 100 peaks. BB' will vary within a similar range. Let us say that the number of cycles sought after is 50, in which case the number of cycles in the channelled spectrum due to BB', which determines $OPD_2$, will vary between 60 and 150. Reading the channelled spectrum at 2 kHz, will lead to a frequency $f_1$ varying between 20 and 200 kHz and to a frequency $f_2$ varying between 120 and 300 kHz. Axial eye movements will not affect the difference of frequencies $f_2$ and $f_1$. It should also be noticed that such high pitch frequencies cannot be heard, so their presence in the spectrum of measuring signal 7 will not disturb the user.

To produce the difference of frequencies, block 85 is used. This operates like a nonlinear amplifier, producing all possible combinations of periodic signals within signal 7, oscillating at multiple of frequencies $nf_1+mf_2$ where n and m could be any integer number. Block 85 may also contain high pass filters or band pass filters at its entry to reduce the noise and reduce the range of frequencies $f_1$ and $f_2$ applied to its input, as well as a low pass filter at its output, to eliminate the high frequency components. For instance, a doubler followed by a low pass filter, will deliver the difference of frequencies $f_1$ and $f_2$.

Figure 12:
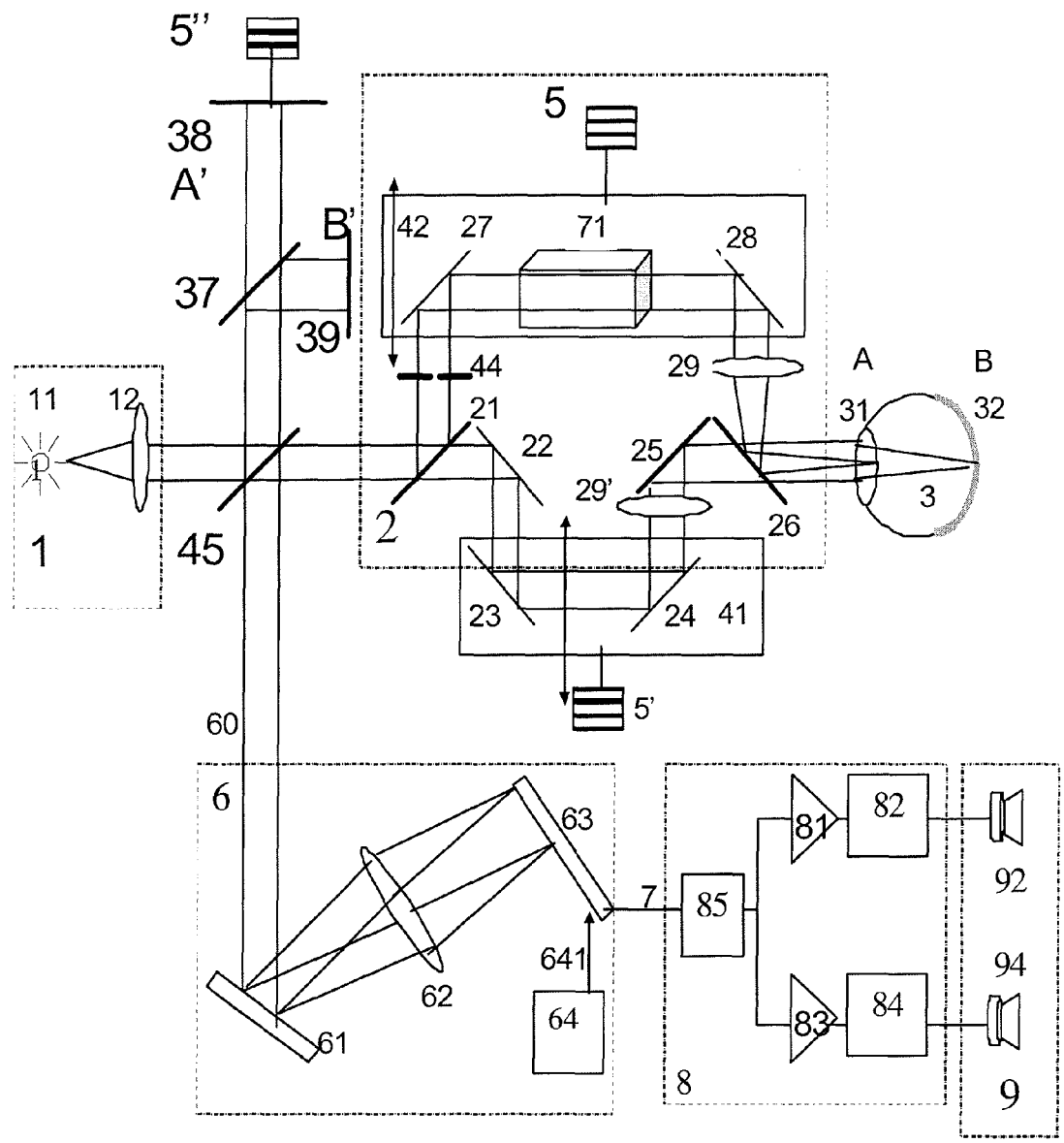
FIG. 12 illustrates an embodiment using a two interferometer configuration and FD-LCI.
Figure 13:
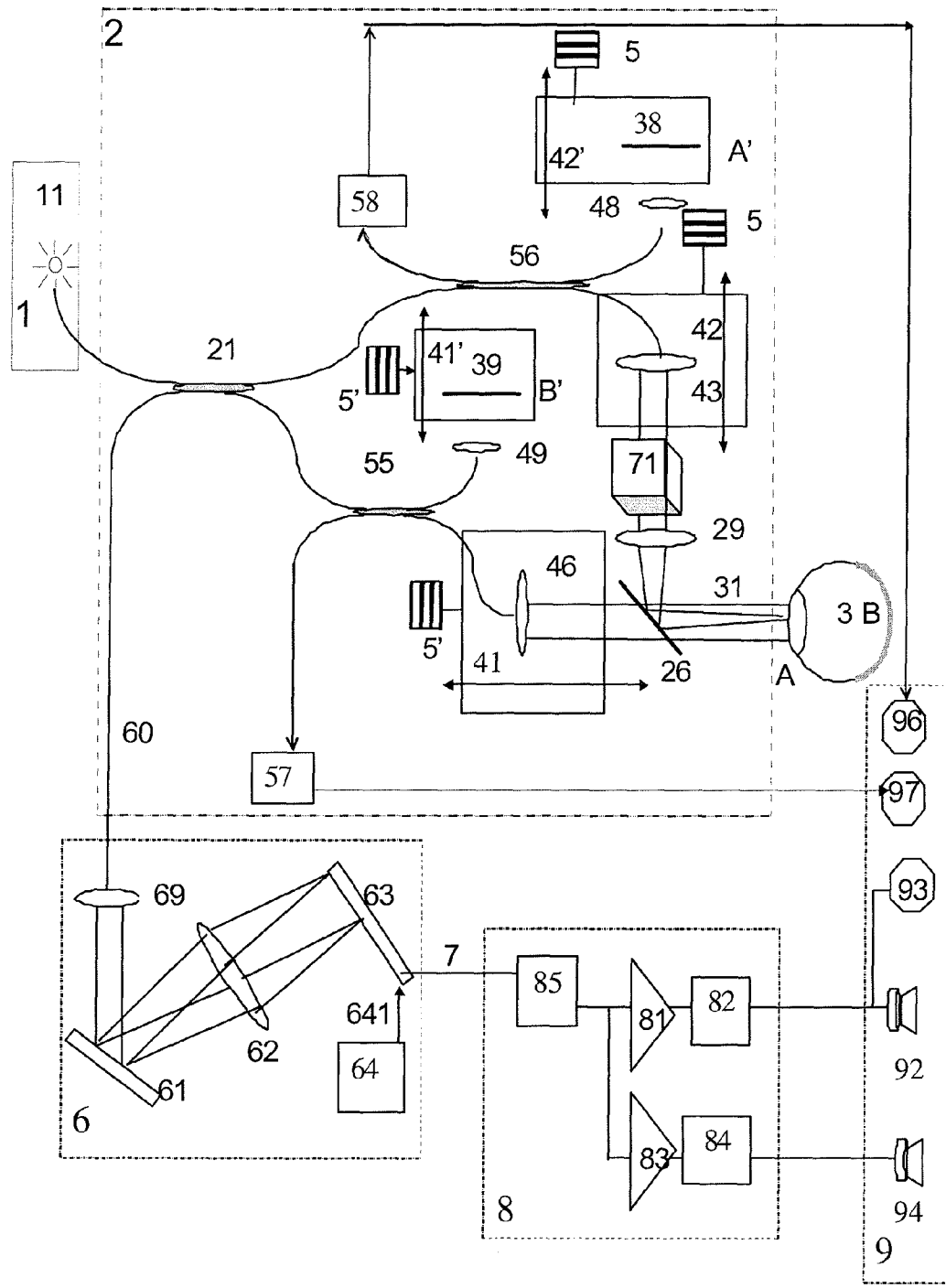
FIG. 13 illustrates another version of an embodiment using a two interferometer configuration and FD-LCI.

Another version of the embodiment in FIG. 12 is that shown in FIG. 13. The interferometer configuration consists in two independent interferometers and where the two output optical signals of each interferometer, are both sent within signal 60, to a single spectral interrogating unit, a spectrometer in the spectral interrogator 6. The reference mirrors 38 and 39, for A' and B', are mounted on translation stages, 42' and 41' behind lenses 48 and 49 respectively. Interference between A and A' is produced in splitter 56 and between B and B' in splitter 55. Measurement is performed only after sufficient strength of signal is obtained in photodetectors 57 and 58, due to the weak signals from the object, 32 and 31 (points B and A respectively).

Figure 14:
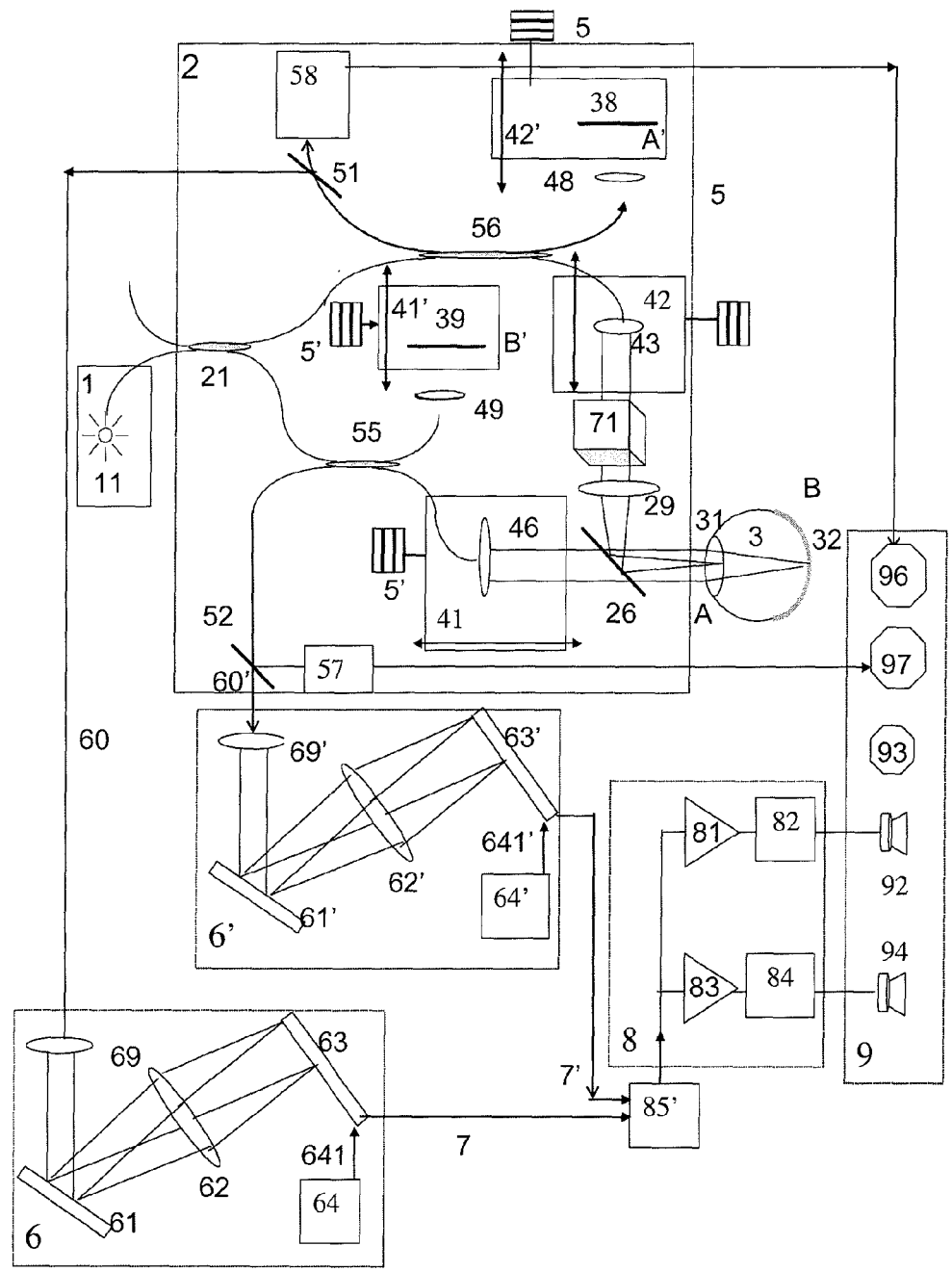
FIG. 14 illustrates an embodiment of the invention using two independent interferometers and two FD-LCI spectral interrogating units.

Another version of the embodiment in FIG. 13 is presented in FIG. 14. Here, the interferometer configuration uses two independent interferometers, each delivers an output optical signal, 60 and 60', to separate spectral interrogating units, 6 and 6', acting as the spectral interrogator, using spectrometers equipped with diffraction gratings, 63 and 63' respectively. In this case, the reading of the two channelled spectra is performed separately. The measuring signals 7 and 7' output of the two spectral interrogating units pulsate at frequencies $f_1$ and $f_2$ respectively. A two input mixer 85' is used to mix the two signals output of spectrometers. Small parts of the interference signals are diverted by splitters 51 and 52 towards photodetectors 58 and 57.

Figure 15:
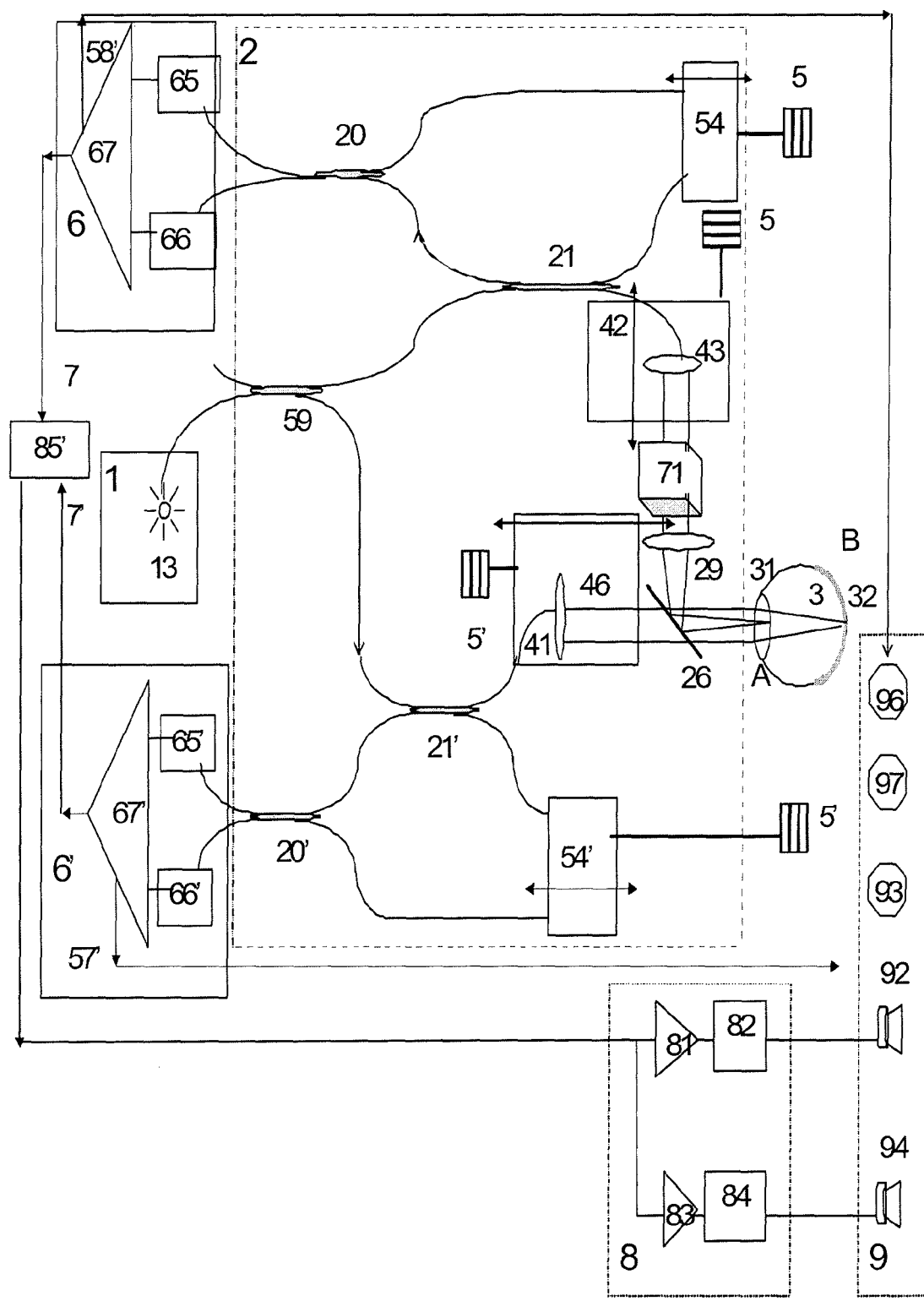
FIG. 15 illustrates an embodiment of the invention using two independent interferometers and two SS-LCI spectral interrogating units.

A similar embodiment can be implemented using the SS-LCI principle, as disclosed in FIG. 15, where a swept narrow band optical source 13 is employed. An interferometer configuration made from two independent interferometers is used. Light is fed via splitter 59 to two independent interferometers, equipped with splitters 21 and 20, respectively 21' and 20'. Delay elements 54 and 54' contain an adjustable delay line to recirculate the reference beam in each interferometer to implement balance detection in balanced splitters 20 and 20'. Delay block 54 compensates for the air delay up to A, point 31. Delay block 54 acts as reflector A' and replaces the translation stage 42' in the embodiments in FIGS. 13 and 14. Delay block 54' acts as reflector B' and replaces the translation stage 41' in the embodiments in FIGS. 13 and 14. Recirculation of the reference beams along blocks 54 and 54' is similar to that used in the embodiment in FIG. 4. These blocks contain similar components, such as a translations stage 4, mirrors 41 and 41, converging elements 23 and 23' and dispersion compensating element 71. The spectral interrogator is made from two spectral interrogating units 6 and 6', each uses balanced photodetection and delivers each, a measuring signal 7 of frequency $f_1$ and a measuring signal 7' of frequency $f_2$ to the two inputs of the mixer 85'. This contains a low pass filter that delivers a signal whose frequency pulsates at the difference between $f_1$ and $f_2$.

Linearity

A problem for both FD-LCI in the embodiments in FIGS. 2, 6, 7, 8, 11, 12, 13 and 14 as well as for the SS-LCI embodiments in FIGS. 4, 9, 10 and 15 is that the AF spectrum of the signal delivered by the electronic processing unit, 8, is wide, unless the reading of the CCD (CMOS) array 63 (63') and that, of the photodetection units 65 (66) is linearised in relation to the optical frequency. Several methods have been proposed, where the data is digitised, zero-padded and only then a FFT is calculated. Such procedures are known for the person skilled in the art and can be implemented here as well if digital processing is adapted. FFT processors are now low cost and an initial calibration can instruct the software to be used. However this would involve an extra device and an extra procedure which may increase the cost.

As an inventive low cost solution, the present disclosure proposes a direct provision of a signal linear in optical frequency.

SS-LCI

Figure 16:
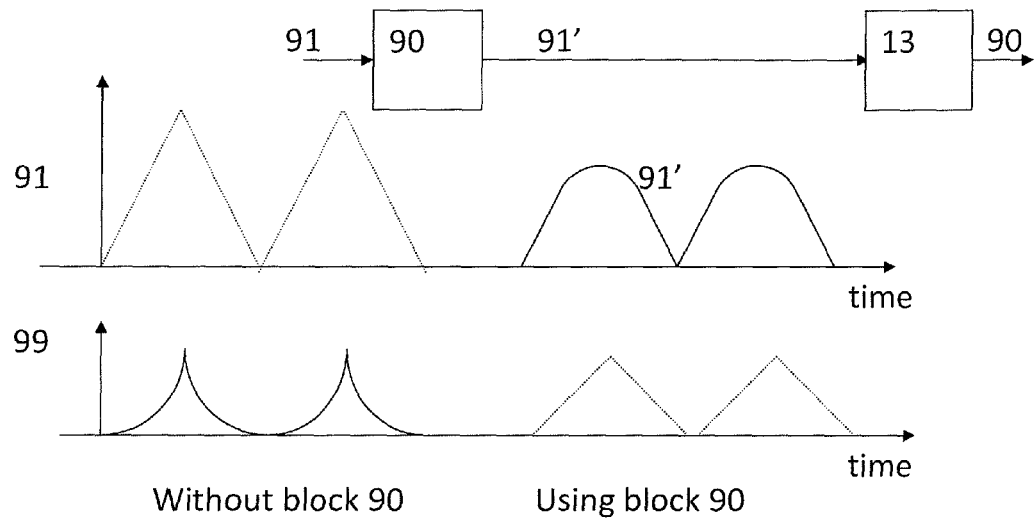
FIG. 16 shows an inventive step on linearization of data from analogue photodetector units used in SS-LCI.

Let us suppose that the tuneable source 13 uses a tunable filter or is a low cost laser diode ramped in current, as reported in the paper by J. Zheng mentioned above. In this case, only a few nanometers tuning bandwidth is achievable, but sufficient to determine a depth resolution better than tens of microns. More expensive sources can be used to achieve micron resolution. In both cases above, either using a tuneable filter in a ring laser or a ramped laser diode, an electrical signal modifies the optical frequency of the output optical signal. In both cases, the output frequency manifests a nonlinear dependence on the electrical input signal, that requires correction. FIG. 16 shows the effect of a nonlinear block 90 on the input voltage, 91 and on the output frequency of the swept source 13, denoted as, 99. When tuning the source 13 in the embodiments in FIGS. 4, 9, 10 and 15, the analogue signal applied to the tuning filter or the laser diode is altered in shape versus time. For instance let us say that the output frequency, 99, of source 13 varies faster than linearly as the controlling voltage increases, as shown in the bottom left in FIG. 16, due to a linear ramp, 91, as shown in the middle of FIG. 16 left. The frequency 99 of the tuneable source 13 would be nonlinear, as shown by the lower inset left, if 91 was employed. A simple nonlinear electric circuit, 90, using diodes can be used to transform the triangle shaped voltage applied to the tuning filter or laser diode, into a nonlinear shape, 91', as shown in FIG. 16 middle right. In this way, dependence of the frequency 99 of the optical signal emitted by 13, versus time approaches linearity, as shown in the right bottom inset.

FD-LCI

Normally, the CCD (CMOS) arrays are read using shift registers where data is shifted to the output linearly in time, pixel by pixel. Such arrays are read using a regular clock which feeds the shift register which controls the successive reading of pixels. It is proposed here that the clock period is altered from a time slot to the next. By successively reducing or increasing the time slot of clock time interval, during the reading time $T_R$ (adjusted for quieter spectrum to 1/F as shown in FIG. 3B), the nonlinear spread of optical frequencies over the linear array can be compensated for.

Figure 17:
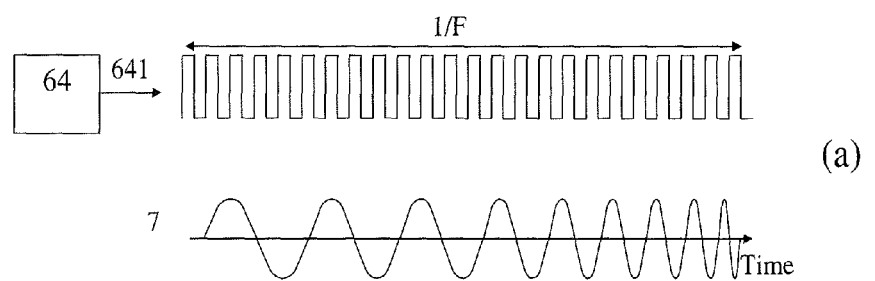
FIG. 17 shows an inventive step on linearization of data from a photodetector array used in FD-LCI.
Figure 17:
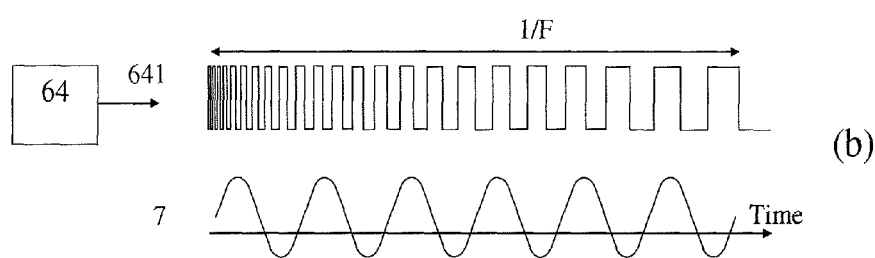

Let us consider a single reflector in the object, 3. FIG. 17(*a*) illustrates the prior art, where the output signal, 7, is a nonlinear sinusoidal signal with nonconstant repetition frequency due to nonlinear dependence of optical frequency along the photodetector array 63, when read by a regular clock signal 641. As an example here, it is considered that from left to right, the frequency of the signal 7 increases. The inventive step is presented in FIG. 17*b*, where 64 is a nonlinear clock generator, as illustrated, the TTL or ECL clock signal exhibits a nonlinear variation of its period during the reading interval of the array 63. Such a nonlinear clock alters the timing when each pixel in the array 63 is transferred out to signal 7. For the case shown in FIG. 17*a*, by reducing the clock period at the beginning of the reading time, the shift register will transfer the arrays charge from the beginning of the array quicker than when using the regular clock in FIG. 17*a*. Then, by the end of the reading time 1/F, the transfer is slowed down by increasing the period of the clock 641. By nonlinearly changing the time interval the array cells are read out from one cycle to the next, the output of the array becomes a clear undistorted sinusoidal signal 7, whose spectrum presents a narrower better spectrally defined frequency component.

For each integration cycle, 1/F, pixel data is taken out using the nonlinear clock 641.

The novel procedures according to the invention help increasing the amplitude of the measuring signal 7 and in consequence, the sensitivity of the set-ups, either FD-LCI or SS-LCI. The larger the reference OPD value established for measurements, $OPD_{ref}$, the better the improvement brought by applying the methods described in FIGS. 16 and 17. In case that $OPD_{ref}$ is chosen at small values, then linearization of data is not necessary, or alternatively, the linearization does not need to be perfect to achieve sufficient enhancement of the signal. In both cases in FIGS. 16 and 17, linearization of data versus optical frequency is performed by altering the speed of reading the channelled spectrum within each period, 1/F, of such reading. When using the linear array in FD-LCI, its reading is altered by modifying the moment when signal from a given photo-site is taken out within the scanning period, using a nonlinear clock 641. When using the swept source in SS-LCI, the reading is altered by modifying the voltage shape, 91', which controls the moment a certain frequency is created, again, within the cycle 1/F.

Figure 18:
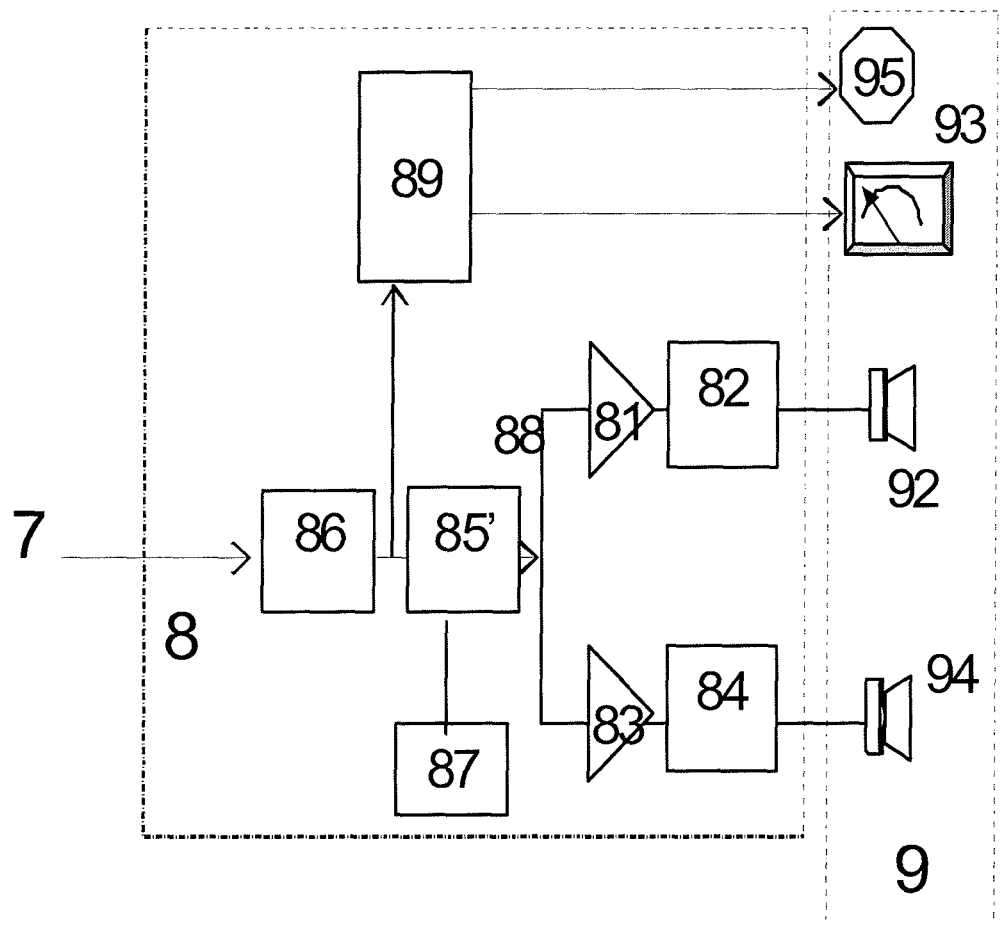
FIG. 18 shows an improved diagram for the electronic processing unit. Components which are the same in the various figures have been designated by the same numerals for ease of understanding.

FIG. 18 presents an improved embodiment of the electronic processing unit 8. All its building parts or only some can be electively used in any of the previous embodiments.

As a first improvement, because the channelled spectrum reading frequency F, may be in the audible range, a rejection filter, 86, is placed on the signal 7, before being sent to band pass filters 82 and 84.

As another possible improvement, the signal output of the rejection filter, 86, is beaten with a locally generated signal. This is especially useful when the frequency f of the measuring signal 7 is larger than the maximum audible frequency, let us say of $f_{amax}=20$ kHz. A beating sound, 88, is produced by beating the signal 7 coming out of the spectral interrogator 6 with a sinusoidal signal of a chosen frequency, G, generated by a signal generator 87, using a two inputs mixer 85'. For instance, let us consider that the reading of the channelled spectrum is performed at F=1 kHz and that the spectral interrogator, 6, has the resolution to read up to 200 peaks in the channelled spectrum. This would lead to a range of frequencies for the signal 7 between F and 200 kHz, where at the maximum it would correspond to an OPD value of approximately $OPD_{max}=200l_c$. Let us say that the sought after OPD value of interest, $OPD_{ref} \square 301_c$. For this OPD value, the channelled spectrum contains 30 peaks and therefore the signal 7 oscillates at $f_{ref}=30F=30$ kHz, larger than $f_{amax}$. The generator 87 is adjusted to deliver a sinusoidal signal of frequency $G=f_{ref}$ and therefore the frequency at the output of 85' is $f_{85'}$=modulus of f−G, |f−G|. In this way, when the OPD is increased from minimum value, $OPD_{min}$, the frequency of the signal out of 85' decreases from 30 kHz to zero when OPD reaches the value of reference, $OPD_{ref}$, and increases again from zero to 200−30=170 kHz, if continuing to increase the OPD up to the maximum axial range, $OPD_{max}$. In this way, the process of searching for the desired audio signal requires bringing $f_{85'}$, i.e. the audio frequency to zero. The range of OPD values where the frequency $f_{85'}$=|f−G| is within the audible range would be for a change in the number of peaks in the channelled spectrum by $f_{amax}/F=20$ from the number of peaks corresponding to the $OPD_{ref}$. This corresponds to a range of peaks in the channelled spectrum from $f_{amax}/F−OPD_{ref}/l_c=30−20=10$ to $f_{amax}/F+OPD_{ref}/l_c=30+20=50$, i.e. to $201_c$, either side of the sought after value, i.e. an interval of $401_c$ out of a total range of 200 $l_c$, which would be a large error. However, this range can be drastically reduced to that given by hearing 100 Hz either side of the zero frequency and optimum adjustment, i.e. to a 20 kHz/(100 Hz)=1/200 range from the case before, i.e. of $0.21_c$, which would be more acceptable.

A more refined adjustment can now be devised. Because the process of deciding exactly where the frequency of signal 88 reaches zero is affected by errors, the OPD value is adjusted by knobs 5 or 5' until the frequency of signal 88 reaches, let us say 1 kHz. The band pass filter 82 is tuned on 1 kHz and drives an LED, 93' or an analogue ammeter, 95' and maxima are achieved for two positions of the adjusting means corresponding to two OPD values shown by the measuring means, 5, as $E_1$ and $E_2$. Let us say that OPD is continuously increased and $E_1$ corresponds to the first value of OPD when 1 kHz is obtained, then the frequency of signal 88 decreases, goes through zero and by continuing the increase in the OPD, the frequency of signal 88 increases from zero to 1 kHz at $E_2$. Then, the unknown length can be determined more exactly, as $(E_1+E_2)/2$, which approximates $OPD_{ref}$. This procedure can be applied to any previously presented embodiment.

A frequency to amplitude converter, 89 could drive another needle meter, 95', or a digital meter, or a display unit, 93', where the colour suggests the strength of the signal. This is useful when the frequency of the measuring signal 7 is higher than the audible range and when using the mixer 85' which provides the same pitch, irrespective if the frequency of the signal 7 is lower or higher than the frequency of the signal generated by generator 87. The frequency to amplitude convertor 89 helps the user understand the absolute direction of OPD change while following the pitch of sound emitted by 94 after mixer 85'.

Stethoscope

A related application is that of monitoring the movement of heart walls in organisms. Such organisms could be larvae, embryos, animals, humans. The beating rate can be easily translated into sound.

Let us consider that in a fly embryo, the heart, object 3 in the embodiments above, moves by 100 microns. Due to a limited number of pixels in the array 63, or limited number of frequency steps in the tuning of the frequency of the optical source, 13, the axial range of the FD-LCI system is limited. Let us say that the axial range is limited to 1 mm. For a coherence length of 10 microns, an OPD=1 mm will create 100 peaks in the channelled spectrum while the heart movement will correspond to a change in the number of peaks by 10. For a reading of the linear array 63 at 20 kHz (selected higher than the maximum audible frequency), the frequencies generated by reading the array 63 will be from 20 kHz to 2 MHz. The heart wall 3 may be at any OPD value within the 1 mm range, let us say that it is in the middle, at 0.5 mm, i.e. the frequency generated during the channelled spectrum reading is 1 MHz. A 100 microns change in the OPD due to the heart wall movement will lead to a change in the frequency of 1 MHz by approximately 200 kHz (a change of $100/l_c=10$ peaks, read at 20 kHz). Beating the photodetector array signal, 7, with a sinusoidal signal generated by 87, of $F_{ref}=1$ MHz, in the mixer 85', will lead to a signal 88, pulsating at a frequency difference of 0 to 200 kHz. When fed to loudspeakers, 92 and 94, a variable pitch will be heard, with frequencies from zero to 20 kHz and pauses due to the inaudible frequencies 20-200 kHz, while 92 will deliver blips of low pitch when the frequency coincides to that of the narrow band filter 82, with pauses followed again by the same succession of frequencies when the heart returns to the initial position. If the embryo 3 moves axially to a different settled axial position, by changing the value of frequency G, the new position is identified and monitoring can start again. The process of retuning G is here equivalent to finding the new axial position of the gate in TD-LCI.

Operating Room

Any of the previous embodiments can be used to assist different interventions in the operating room. For instance, ablation of a bone and thickness adjustment can be monitored using sound, its intensity and pitch. The surgeon mainly focuses on the point of ablation, on the surrounding tissue and an apparatus according to the inventions provides other guiding information.

OCT

To all embodiments above, a transversal scanning head, to deflect the object beam in a raster fashion, can be added. In this case, the user can measure variation of thickness of the object within its transversal surface. Ablation or drop of a solvent can affect such thickness and this can be easily compared from point to point by following the pitch of the sound during scanning. For instance, scanning a line in 1 second, allows continuous observation of sound. In 10-50 seconds all object is scanned, in 10 to 50 lines. Exact measurement of thickness may not be necessary, while relative variations of thickness within the transversal section are easily distinguished from the sound pitch variation.

For enhanced sensitivity, the blocks 81 and 83 can be equipped with zero crossing circuits. Such circuits generate a narrow pulse anytime the incoming signal crosses the voltage value of zero. This can then be transformed into a sinusoidal signal with repetition frequency determined by the inverse of time interval from a zero crossing to the next. In this way, the frequency of the signal heard in 92 and 94 is strictly proportional to the repetition in the channelled spectrum and the signal amplitude does not depend on the amplitude of the channelled spectrum. Sometimes, without such zero crossing circuits, the modulation amplitude of the channelled spectrum is so high that saturation may occur which will distort the sound produced by the loudspeakers 92 and 94. Irrespective of the amplitude of the incoming signal, the zero crossing sensing blocks 81, 83, will generate signals of constant amplitude and frequency depending on the repetition of the input signal only.

Obviously, for those skilled in the art, where splitters are in bulk, they could equally be in fiber and vice versa. Focusing elements throughout the disclosure could be curved mirrors or lenses.

Thus, it has been apparent that there has been provided, in accordance with the present invention an apparatus which fully satisfies the means, objects and advantages set forth hereinbefore.

Therefore, having described specific embodiments of the present invention, it will be understood that alternatives, modifications and variations thereof may be suggested by those skilled in the art.

The invention claimed is:

1. Spectral interferometry apparatus comprising:
    an optical source;
    an interferometer configuration having at least an interferometer equipped with at least two optical paths, having an interferometer output, wherein the optical spectrum at the interferometer output is modulated, with modulation depending on the optical path difference (OPD) in the interferometer;
    a spectral interrogator configuration equipped with at least a spectral interrogating unit, for the spectrum at the output of the interferometer which reads the spectrum with a periodicity 1/F and delivers a measuring signal to
    an electronic processing unit which provides a variable signal with a dominant single frequency in response to the modulation of the optical spectrum, to an indicating means, where the indicating means provides an indicating signal in the form of an audio signal, of a luminous signal, or a combination of both;
    wherein at least a characteristic of the indicating signal provides a measurement of a single OPD value in the interferometer configuration.

2. Spectral interferometry apparatus according to claim 1, wherein the measuring means, is a micrometer screw, a graded knob or a sliding ruler.

3. Spectral interferometry apparatus according to claim 1, wherein the optical source is broadband; and the spectral interrogating unit comprises a spectrometer equipped with a linear photodetector array scanned at a frequency F to provide the measuring signal.

4. Spectral interferometry apparatus according to claim 1, wherein the optical source is a narrow band swept source, and the spectral interrogating unit is equipped with at least a photodetecting unit which provides a measuring signal while tuning the optical source at rate F.

5. Spectral interferometry apparatus according to claim 1, where the interferometer configuration consists in two independent interferometers, where a $1^{st}$ interferometer consists in:
    (i) a $1^{st}$ interface optics to collect light from point A to form an object beam of the $1^{st}$ interferometer
    (ii) a $1^{st}$ reference optics to form a $1^{st}$ reference beam and where the optical path between the lengths traversed by the two beams in the $1^{st}$ interferometer is $OPD_1$,
    a 2nd interferometer that consists in
    (i) a 2nd interface optics to collect light from point B to form an object beam of the 2nd interferometer
    (ii) a 2nd reference optics to form a $2^{nd}$ reference beam and where the optical path between the lengths traversed by the two beams in the 2nd interferometer is $OPD_2$,
    and where the output optical signals of the two interferometers are independent of each other and are each sent to a separate output optical signal of the said interferometer configuration, and
    where the spectral interrogator configuration consists in two spectral interrogator units, processing independently and simultaneously the output optical signal from $1^{st}$ interferometer and the output optical signal from $2^{nd}$ interferometer and where a $1^{st}$ spectral interrogating unit generates a measuring signal of frequency $f_1$ for the output signal from the $1^{st}$ interferometer, and a $2^{nd}$ spectral interrogating unit generates a measuring signal of frequency $f_2$ for the output signal from the 2nd interferometer and
    where the electronics processing unit further contains a two input mixer followed by a low pass filter which receives the two measuring signals and provides an indicating signal of frequency $|f_1-f_2|$.

6. Spectral interferometry apparatus according to claim 5, wherein the indicating means comprises a luminous emitter and the characteristic of the said indicating signal is the intensity of the light emitted by the luminous emitter, its pulsation frequency or its colour.

7. Spectral interferometry apparatus according to claim 1 where the electronic processing unit is equipped with at least a band-pass filter which is tuned on a frequency within the audible range delivered to the indicating means, which determines as a characteristic of the indicating signal its pitch.

8. Spectral interferometry apparatus according to claim 1 where the electronic processing unit is equipped with a frequency to amplitude convertor which translates the frequency of the said measuring signal into amplitude as a characteristic of the indicating signal.

9. Spectral interferometry apparatus according to claim 3, where the linear photodetector array is read using a clock pulse with variable time interval between successive pulses and where the time interval between clock pulses is altered in such a way as to produce a linear dependence between the moment of time a pixel is read and an optical frequency a spectrum of an optical signal output at the inteferometer output.

10. Spectral interferometry apparatus according to claim 4, where the said swept source is controlled by a voltage source, wherein the voltage source is arranged to produce a voltage signal that during the tuning cycle 1/F has a voltage versus time variation distorted in such a way so that the optical frequency of the swept source varies linearly in time.

11. Spectral interferometry apparatus claim 1, wherein the adjusting length device is a translation stage, equipped with a knob or a cursor, where the translation stage is moved by actuating on the knob or the cursor and the knob or the cursor are marked with divisions or the stage is equipped with a ruler, and where the positions of the stage can be identified from the divisions of the knob, cursor or ruler, and where the translation stage carries elements parts of the interferometer which determine a change in the optical path travelled by light.

12. Spectral interferometry apparatus according to claim 1 employed on measuring an unknown length between a first point, A, and a second point, B, where point A is placed on or in an object, and the point B is either is placed inside the apparatus or on the bottom part of the object, the apparatus further comprising:

an adjusting length device arranged to change the length of at least one of the optical paths of the interferometer configuration, the adjusting length device having a measuring means providing a length measurement of the at least one optical path, and wherein the spectral interferometry apparatus is arranged to perform the measurement of the unknown length between A and B by actuating on the adjusting length device until a characteristic of the indicating signal reaches a desired value and the value of the unknown length is obtained from the indication of the measuring means.

13. Spectral interferometry apparatus according to claim 12 wherein point B is the bottom part of an object and the unknown distance is the thickness, E of the object measured between A and B.

14. Spectral interferometry apparatus according to claim 13, wherein the said object is the eye and the unknown length, between A and B, is the eye length.

15. Spectral interferometry apparatus according to claim 13, where the interferometer configuration consists in:
   (i) an interface optics equipped with a $1^{st}$ splitter, which collects returned signals from both points A and B and where the two beams from A and B define a two beam sensing interferometer, and the difference of optical path travelled roundtrip by light from the $1^{st}$ splitter to A and from $1^{st}$ splitter to B defines an $OPD_1$, and
   (ii) an adjustable two beam interferometer, whose optical path difference measured between its path lengths is $OPD_2$, and where the said adjusting length device in claim 1 is used to alter $OPD_2$,
   and where the sensing interferometer and the adjustable two beam interferometer are connected in series, to provide the output optical signal to the said spectral interrogator which produces a measuring signal of frequency f proportional to the difference between $OPD_1$ and $OPD_2$.

16. Spectral interferometry apparatus according to claim 13, where the interferometer configuration consists in two interferometers, where a $1^{st}$ interferometer consists in:
   (i) a $1^{st}$ interface optics to collect light from point A to form an object beam of the $1^{st}$ interferometer
   (ii) a $1^{st}$ reference optics to form a $1^{st}$ reference beam
   and where the optical path between the lengths traversed by the two beams in the $1^{st}$ interferometer is $OPD_1$,
a 2nd interferometer that consists in
   (iii) a 2nd interface optics to collect light from point B to form an object beam of the 2nd interferometer,
   (ii) a 2nd reference optics to form a $2^{nd}$ reference beam
   and where the optical path between the lengths traversed by the two beams in the 2nd interferometer is $OPD_2$,
   and where the output optical signals of the two interferometers are both present in the said output optical signal of the interferometer configuration, and
where the spectral interrogator configuration generates a measuring signal of frequency $f_1$ for the output signal from the $1^{st}$ interferometer and a measuring signal of frequency $f_2$ for the output signal from the 2nd interferometer and where
the electronics processing unit further contains a nonlinear amplifier followed by a low pass filter which provides an indicating signal of frequency $|f_1-|f_2$.

17. Spectral interferometry apparatus according to claim 1, wherein the electronic processing unit further comprises an amplifier of the measuring signal and a rejection filter tuned on the frequency F, and a band-pass filter tuned on a reference frequency within the audible range.

18. Spectral interferometry apparatus according to claim 1 where the electronic processing unit is equipped with a nonlinear amplifier, a thresholding circuit and/or a zero crossing circuit.

19. Spectral interferometry apparatus according to claim 1, wherein the electronic processing unit is equipped with at least a device from the category of a nonlinear amplifier, a thresholding circuit, a zero crossing circuit and a rejection filter tuned on the frequency F.

20. Spectral interferometer according to claim 1 wherein within the measuring signal, the readout time $T_R$ of the optical spectrum is adjusted to be as close as possible to 1/F.

21. Spectral interferometry apparatus according to claim 1, wherein the indicating means contains at least a device from the category of loudspeaker or a earphone and the characteristic of the said indicating signal is the intensity of the sound emitted or its pitch or both.

* * * * *